(12) United States Patent
Tanaka et al.

(10) Patent No.: US 9,879,274 B2
(45) Date of Patent: Jan. 30, 2018

(54) PLANT SUITABLE FOR INCREASING PRODUCTION OF PHLOEM TISSUE AND USE OF SAME

(71) Applicant: KABUSHIKI KAISHA TOYOTA CHUO KENKYUSHO, Nagakute-shi, Aichi-ken (JP)

(72) Inventors: Tomoko Tanaka, Nagakute (JP); Hiroki Sugimoto, Nagakute (JP); Ritsuko Yogo, Nagakute (JP); Nobuhiko Muramoto, Nagakute (JP); Norihiro Mitsukawa, Nagakute (JP); Kazufumi Tabata, Chiryu (JP)

(73) Assignee: KABUSHIKI KAISHA TOYOTA CHUO KENKYUSHO, Nagakute-shi (JP)

( * ) Notice: Subject to any disclaimer, the term of this patent is extended or adjusted under 35 U.S.C. 154(b) by 233 days.

(21) Appl. No.: 14/481,309

(22) Filed: Sep. 9, 2014

(65) Prior Publication Data

US 2015/0074848 A1     Mar. 12, 2015

(30) Foreign Application Priority Data

Sep. 10, 2013  (JP) .................................. 2013-187742

(51) Int. Cl.
*A01H 5/00*       (2006.01)
*C12N 15/82*      (2006.01)

(52) U.S. Cl.
CPC ..... *C12N 15/8261* (2013.01); *C12N 15/8223* (2013.01)

(58) Field of Classification Search
None
See application file for complete search history.

(56) References Cited

U.S. PATENT DOCUMENTS

| 8,247,646 | B2 | 8/2012 | Guo et al. | |
| 2003/0159180 | A1* | 8/2003 | Fischer | C12N 15/8289 800/287 |
| 2007/0039070 | A1 | 2/2007 | Bloksberg et al. | |
| 2009/0229008 | A1 | 9/2009 | Bloksberg et al. | |
| 2011/0065583 | A1* | 3/2011 | Kondo | A01N 37/46 504/320 |
| 2011/0078818 | A1 | 3/2011 | Kondo et al. | |
| 2012/0005787 | A1 | 1/2012 | Kondo et al. | |
| 2012/0084885 | A1* | 4/2012 | Alexandrov | C12N 15/8216 800/298 |
| 2012/0137385 | A1 | 5/2012 | Bloksberg et al. | |

FOREIGN PATENT DOCUMENTS

| JP | A-2002-534078 | 10/2002 |
| JP | A-2010-207199 | 9/2010 |
| JP | 2011-055780 A | 3/2011 |
| JP | A-2011-229530 | 11/2011 |
| WO | WO 00/40694 | 7/2000 |
| WO | WO 2009/113684 | 9/2009 |

OTHER PUBLICATIONS

Fisher et al. (Current Biology, 17:1061-1066; Published Jun. 19, 2007).*
Truernit et al. (Planta, 196:564-570, 1995).*
Hu et al., "The Arabidopsis Auxin-Inducible Gene ARGOS Controls Lateral Organ Size," *The Plant Cell*, vol. 15, Sep. 2003, pp. 1951-1961.
Mizukami et al., "Plant Organ Size Control: Aintegumenta Regulates Growth and Cell Numbers During Organogenesis," *PNAS*, vol. 97, No. 2, Jan. 2000, pp. 942-947.
Jun. 20, 2017 Office Action issued in Japanese Patent Application No. 2013-187742.
Funada, Ryo. "Control Mechanism of Woody Biomass Formation—Division and Differentiation of Tree Cells". Bioscience Seminar No. 840, The Tokyo University Graduate School of Science Department of Biological Sciences, 2007.
Wenzel, Carol L. et al. "Identification of Genes Expressed in Vascular Tissues Using NPA-Induced Vascular Overgrowth in Arabidopsis". Plant Cell Physiology, vol. 49, No. 3, pp. 457-468, 2008.
Schweighofer, Alois et al. "Plant PP2C Phosphatases: Emerging Functions in Stress Signaling". Trends in Plant Science, vol. 9, No. 5, pp. 236-243, 2004.

* cited by examiner

*Primary Examiner* — Vinod Kumar
(74) *Attorney, Agent, or Firm* — Oliff PLC

(57) ABSTRACT

A method for producing a plant includes growing a plant from plant cells in which a promoter and a coding sequence under the control of the promoter have been artificially introduced; and selecting the plant in which an amount of phloem tissue is increased 2.0 times or more in comparison with a wild type plant of the same species. The promoter is a promoter for a gene encoding a protein having at least 60% identity with the amino acid sequence of tracheary element differentiation inhibitory factor (TDIF) receptor (TDR) of *Arabidopsis thaliana*. The coding sequence encodes either (i) a protein having three common sequences composed of the amino acid sequences of SEQ ID NOS: 1 to 3 in this order starting from the N-terminal side, or (ii) a protein having 95% or more identity with the amino acid sequence of SEQ ID NO:5.

8 Claims, 5 Drawing Sheets

```
SEQUENCE LISTING

<160> NUMBER OF SEQ ID NOS: 25

<210> SEQ ID NO 1
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K, R, Q or N
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

Xaa Xaa Gly Xaa Phe Asp Gly His Gly Xaa Xaa Gly Xaa Xaa Xaa Xaa
1               5                   10                  15

Xaa Xaa Val

<210> SEQ ID NO 2
<211> LENGTH: 27
```

```
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
<223> OTHER INFORMATION: Xaa can be any naturally occurring amino acid,
      or preferably V, L or I
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid,
      or preferably I, V, F, M or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid,
      or preferably G or A
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably L, V or I
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I
```

<400> SEQUENCE: 2

Ser Gly Xaa Thr Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25

<210> SEQ ID NO 3
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably M, V or F
<220> FEATURE:
<221> NAME/KEY: misc_feature
<222> LOCATION: (5)..(5)
<223> OTHER INFORMATION: Xaa can be any naturally occurring amino acid,
      or preferably S, A or T
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
      or preferably F, I or V
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid,
      or preferably K or E
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,

```
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid,
      or preferably D, N or H
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or F
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (38)..(38)
<223> OTHER INFORMATION: Xaa can be any naturally occurring amino acid,
      or preferably L or V
<220> FEATURE:
<221> NAME/KEY: misc_feature
<222> LOCATION: (40)..(40)
<223> OTHER INFORMATION: Xaa can be any naturally occurring amino acid,
      or preferably T or S
<220> FEATURE:
<221> NAME/KEY: misc_feature
<222> LOCATION: (43)..(43)
<223> OTHER INFORMATION: Xaa can be any naturally occurring amino acid,
      or preferably V, I or M
<220> FEATURE:
<221> NAME/KEY: misc_feature
<222> LOCATION: (44)..(44)
<223> OTHER INFORMATION: Xaa can be any naturally occurring amino acid,
      or preferably W or F
<220> FEATURE:
<221> NAME/KEY: misc_feature
<222> LOCATION: (45)..(45)
<223> OTHER INFORMATION: Xaa can be any naturally occurring amino acid,
      or preferably D or E
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid,
      or preferably L, I or M
<220> FEATURE:
<221> NAME/KEY: misc_feature
```

```
<222> LOCATION: (48)..(48)
<223> OTHER INFORMATION: Xaa can be any naturally occurring amino acid,
      or preferably S, T or P
<220> FEATURE:
<221> NAME/KEY: misc_feature
<222> LOCATION: (49)..(49)
<223> OTHER INFORMATION: Xaa can be any naturally occurring amino acid,
      or preferably N or S
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid,
      or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
      or preferably L, V, I or M
<220> FEATURE:
<221> NAME/KEY: misc_feature
<222> LOCATION: (56)..(56)
<223> OTHER INFORMATION: Xaa can be any naturally occurring amino acid,
      or preferably I or V

<400> SEQUENCE: 3

Gly Xaa Ala Xaa Xaa Arg Xaa Xaa Gly Asp Xaa Xaa Xaa Xaa Xaa Xaa
1               5                   10                  15

Gly Xaa Xaa Xaa Xaa Pro Xaa Xaa Xaa Xaa Xaa Xaa Xaa Xaa Xaa Xaa
            20                  25                  30

Xaa Xaa Xaa Xaa Xaa Xaa Ala Xaa Asp Gly Xaa Xaa Xaa Xaa Xaa Xaa
        35                  40                  45

Xaa Xaa Xaa Xaa Xaa Xaa Xaa Xaa
    50                  55

<210> SEQ ID NO 4
<211> LENGTH: 358
<212> TYPE: PRT
<213> ORGANISM: Arabidopsis thaliana

<400> SEQUENCE: 4

Met Gly His Phe Ser Ser Met Phe Asn Gly Ile Ala Arg Ser Phe Ser
1               5                   10                  15

Ile Lys Lys Ala Lys Asn Ile Asn Ser Ser Lys Ser Tyr Ala Lys Glu
            20                  25                  30

Ala Thr Asp Glu Met Ala Arg Glu Ala Lys Lys Lys Glu Leu Ile Leu
        35                  40                  45

Arg Ser Ser Gly Cys Ile Asn Ala Asp Gly Ser Asn Asn Leu Ala Ser
    50                  55                  60

Val Phe Ser Arg Arg Gly Glu Lys Gly Val Asn Gln Asp Cys Ala Ile
65                  70                  75                  80

Val Trp Glu Gly Tyr Gly Cys Gln Glu Asp Met Ile Phe Cys Gly Ile
                85                  90                  95

Phe Asp Gly His Gly Pro Trp Gly His Phe Val Ser Lys Gln Val Arg
            100                 105                 110
```

```
Asn Ser Met Pro Ile Ser Leu Leu Cys Asn Trp Lys Glu Thr Leu Ser
            115                 120                 125

Gln Thr Thr Ile Ala Glu Pro Asp Lys Glu Leu Gln Arg Phe Ala Ile
        130                 135                 140

Trp Lys Tyr Ser Phe Leu Lys Thr Cys Glu Ala Val Asp Leu Glu Leu
145                 150                 155                 160

Glu His His Arg Lys Ile Asp Ser Phe Asn Ser Gly Thr Thr Ala Leu
                165                 170                 175

Thr Ile Val Arg Gln Gly Asp Val Ile Tyr Ile Ala Asn Val Gly Asp
            180                 185                 190

Ser Arg Ala Val Leu Ala Thr Val Ser Asp Glu Gly Ser Leu Val Ala
        195                 200                 205

Val Gln Leu Thr Val Asp Phe Lys Pro Asn Leu Pro Gln Glu Glu Glu
    210                 215                 220

Arg Ile Ile Gly Cys Asn Gly Arg Val Phe Cys Leu Gln Asp Glu Pro
225                 230                 235                 240

Gly Val His Arg Val Trp Gln Pro Val Asp Glu Ser Pro Gly Leu Ala
                245                 250                 255

Met Ser Arg Ala Phe Gly Asp Tyr Cys Ile Lys Asp Tyr Gly Leu Val
            260                 265                 270

Ser Val Pro Glu Val Thr Gln Arg His Ile Ser Ile Arg Asp Gln Phe
        275                 280                 285

Ile Ile Leu Ala Thr Asp Gly Val Trp Asp Val Ile Ser Asn Gln Glu
    290                 295                 300

Ala Ile Asp Ile Val Ser Ser Thr Ala Glu Arg Ala Lys Ala Ala Lys
305                 310                 315                 320

Arg Leu Val Gln Gln Ala Val Arg Ala Trp Asn Arg Lys Arg Arg Gly
                325                 330                 335

Ile Ala Met Asp Asp Ile Ser Ala Val Cys Leu Phe Phe His Ser Ser
            340                 345                 350

Ser Ser Ser Pro Ser Leu
        355

<210> SEQ ID NO 5
<211> LENGTH: 555
<212> TYPE: PRT
<213> ORGANISM: Arabidopsis thaliana

<400> SEQUENCE: 5

Met Lys Ser Phe Cys Asp Asn Asp Asn Asn His Ser Asn Thr Thr
1               5                   10                  15

Asn Leu Leu Gly Phe Ser Leu Ser Ser Asn Met Met Lys Met Gly Gly
                20                  25                  30

Arg Gly Gly Arg Glu Ala Ile Tyr Ser Ser Ser Thr Ser Ser Ala Ala
            35                  40                  45

Thr Ser Ser Ser Val Pro Pro Gln Leu Val Val Gly Asp Asn Thr
        50                  55                  60

Ser Asn Phe Gly Val Cys Tyr Gly Ser Asn Pro Asn Gly Gly Ile Tyr
65                  70                  75                  80

Ser His Met Ser Val Met Pro Leu Arg Ser Asp Gly Ser Leu Cys Leu
                85                  90                  95

Met Glu Ala Leu Asn Arg Ser Ser His Ser Asn His His Gln Asp Ser
            100                 105                 110

Ser Pro Lys Val Glu Asp Phe Phe Gly Thr His His Asn Asn Thr Ser
        115                 120                 125
```

```
His Lys Glu Ala Met Asp Leu Ser Leu Asp Ser Leu Phe Tyr Asn Thr
    130                 135                 140

Thr His Glu Pro Asn Thr Thr Asn Phe Gln Glu Phe Phe Ser Phe
145                 150                 155                 160

Pro Gln Thr Arg Asn His Glu Glu Thr Arg Asn Tyr Gly Asn Asp
                165                 170                 175

Pro Ser Leu Thr His Gly Gly Ser Phe Asn Val Gly Val Tyr Gly Glu
                180                 185                 190

Phe Gln Gln Ser Leu Ser Leu Ser Met Ser Pro Gly Ser Gln Ser Ser
            195                 200                 205

Cys Ile Thr Gly Ser His His Gln Gln Asn Gln Asn Gln Asn His
    210                 215                 220

Gln Ser Gln Asn His Gln Gln Ile Ser Glu Ala Leu Val Glu Thr Ser
225                 230                 235                 240

Val Gly Phe Glu Thr Thr Thr Met Ala Ala Ala Lys Lys Lys Arg Gly
                245                 250                 255

Gln Glu Asp Val Val Val Gly Gln Lys Gln Ile Val His Arg Lys
            260                 265                 270

Ser Ile Asp Thr Phe Gly Gln Arg Thr Ser Gln Tyr Arg Gly Val Thr
    275                 280                 285

Arg His Arg Trp Thr Gly Arg Tyr Glu Ala His Leu Trp Asp Asn Ser
    290                 295                 300

Phe Lys Lys Glu Gly His Ser Arg Lys Gly Arg Gln Val Tyr Leu Gly
305                 310                 315                 320

Gly Tyr Asp Met Glu Glu Lys Ala Ala Arg Ala Tyr Asp Leu Ala Ala
                325                 330                 335

Leu Lys Tyr Trp Gly Pro Ser Thr His Thr Asn Phe Ser Ala Glu Asn
            340                 345                 350

Tyr Gln Lys Glu Ile Glu Asp Met Lys Asn Met Thr Arg Gln Glu Tyr
            355                 360                 365

Val Ala His Leu Arg Arg Lys Ser Ser Gly Phe Ser Arg Gly Ala Ser
        370                 375                 380

Ile Tyr Arg Gly Val Thr Arg His His Gln His Gly Arg Trp Gln Ala
385                 390                 395                 400

Arg Ile Gly Arg Val Ala Gly Asn Lys Asp Leu Tyr Leu Gly Thr Phe
                405                 410                 415

Gly Thr Gln Glu Glu Ala Ala Glu Ala Tyr Asp Val Ala Ala Ile Lys
            420                 425                 430

Phe Arg Gly Thr Asn Ala Val Thr Asn Phe Asp Ile Thr Arg Tyr Asp
        435                 440                 445

Val Asp Arg Ile Met Ser Ser Asn Thr Leu Leu Ser Gly Glu Leu Ala
    450                 455                 460

Arg Arg Asn Asn Asn Ser Ile Val Val Arg Asn Thr Glu Asp Gln Thr
465                 470                 475                 480

Ala Leu Asn Ala Val Val Glu Gly Gly Ser Asn Lys Glu Val Ser Thr
                485                 490                 495

Pro Glu Arg Leu Leu Ser Phe Pro Ala Ile Phe Ala Leu Pro Gln Val
            500                 505                 510

Asn Gln Lys Met Phe Gly Ser Asn Met Gly Gly Asn Met Ser Pro Trp
        515                 520                 525

Thr Ser Asn Pro Asn Ala Glu Leu Lys Thr Val Ala Leu Thr Leu Pro
    530                 535                 540
```

Gln Met Pro Val Phe Ala Ala Trp Ala Asp Ser
545                 550                 555

<210> SEQ ID NO 6
<211> LENGTH: 2060
<212> TYPE: DNA
<213> ORGANISM: Arabidopsis thaliana

<400> SEQUENCE: 6

| | | | | |
|---|---|---|---|---|
| aagaagttga | ttttggactt | ctaattaacc | acacttacaa | agtgattata ttcgaaccaa | 60 |
| tgcagttgca | aactatgatg | caacgggtaa | agaattaacg | atatataata gaaatgaatg | 120 |
| tgtgtgattt | caaatatag | tatagcatta | agctcactca | cgtacgtacg gagtctttaa | 180 |
| gatatgtatg | cataagcgat | aatttaggtg | attagttggg | aaataatgaa ttccttttg | 240 |
| gaactttatg | gatcatcgaa | taaatgtgag | atatttaatt | cacccaacct taatgatgaa | 300 |
| aagtgaatct | ataatggcaa | gcaaccatca | tgatacaaac | cttatatgcc cttaagtcaa | 360 |
| tttctacagc | tataacttta | tatatatagc | attgacaaaa | gataatttat ttttttcatt | 420 |
| gtgttactgt | gtttttagta | aagaaaagaa | aaaatatcat | aagaaataga catcgtgacc | 480 |
| ccaaaaaaaa | tacgtataag | caaaaggcat | agcttggatt | tcctagtagt atcaaataaa | 540 |
| taaatgagac | aaaatatttc | tagtagaacg | ggattacggg | accatgtgtt tgagatattt | 600 |
| tatgaaaatc | aatagaaata | gtaaatgaaa | aaatatgaga | ataaacttg tgttcataat | 660 |
| atgatgatgt | atatacaaga | ttaacatgta | aattaaagaa | tgaagagacc tagctcgaca | 720 |
| cattattttt | agtagagcag | aaccaggtga | ttgagataat | tcatgttcat aattatgaat | 780 |
| tcacgagtaa | ataaactcgt | aaatatcaag | aatgtaagaa | aaacgatttt ttttttcttc | 840 |
| ttcttatagt | agtctaatag | ttgaaagatt | tatcatgtaa | gcgtagaatt taatgttgaa | 900 |
| attatctcac | tacgatttga | atcatgctga | gaattaagct | aatgcttagg atggaatgtt | 960 |
| gtagtctatc | gtataaaata | actttatttt | agactacgat | aaaattaaaa tcataaaact | 1020 |
| ctcaactcca | atcctaatct | aatcaagttt | ttctaaggtt | ggtagacaat agtagatttt | 1080 |
| cagtgatcgt | aagtattact | tggcatatat | ataaacgaac | tgaaaaataa gtcccaatgt | 1140 |
| aatatcattt | cactaaaagt | aataaagaga | tgcacgcgta | tatatctata cgtatgaatg | 1200 |
| gtctgatgaa | aggataaaaa | aagaatggtg | taataaattt | gttataaaat cttgaatctt | 1260 |
| ttaggcgcga | gattgttgtt | cgaaaaaaaa | aaaccgtaat | tcatatatat gtaaaaactt | 1320 |
| atatacgcac | acatatatgt | agtgggcatg | agagttagtg | gagagacaga ggattttagc | 1380 |
| tttattggat | cctgtgagtg | actgggataa | atacagtcca | ctttcgctta ttgtgtatct | 1440 |
| atgtacttgt | acatctgcat | gcgtatacat | tccattgaac | attcaatttg tatgcaaaag | 1500 |
| gttttttaaa | aagaatacca | tagtggaaaa | aaagaatttt | taatgaggag aagaaattaa | 1560 |
| aggacaaaga | aaagatacta | gcaaatctaa | ttaatcggtt | tttaatatga gtggcattgt | 1620 |
| gtgatttggt | ttctgatttt | acccaatact | tgtatgatgg | caaacaaaa acaaaatcta | 1680 |
| caattatagt | atatacgttt | tattttggtt | catacttaat | aaaggtaaca aacagaaaaa | 1740 |
| agtactagta | tacgaagtac | agtaatttga | aaaaagtaag | aaaagtaaaa gaagagtgga | 1800 |
| aaatggattg | agtttttttt | ttctctttgc | ttttgttttc | ttcccacac aaaaaccata | 1860 |
| atgccttaac | caacaaaagc | cagaccatta | gacgcactcc | acaatcatca ccttcatcat | 1920 |
| gacttcttct | tctcttctct | tcttccatct | tcttcttctt | caaacccctta aatccaccat | 1980 |
| tgtcaacact | aacacctttc | tcaacaatat | caccacactt | cctcaaacaa cttcactta | 2040 | atttctttct aaaagctacg                                                2060

<210> SEQ ID NO 7
<211> LENGTH: 2267
<212> TYPE: DNA
<213> ORGANISM: Arabidopsis thaliana

<400> SEQUENCE: 7

```
acgcaaacta actacaacct tcttttgggg tccccatccc cgaccctaat gttttggaat      60
taataaaact acaatcactt accaaaaaat aaaagttcaa ggccactata atttctcata     120
tgaacctaca tttataaata aaatctggtt tcatattaat ttcacacacc aagttacttt     180
ctattattaa ctgttataat ggaccatgaa atcatttgca tatgaactgc aatgatacat     240
aatccacttt gttttgtggg agacatttac cagatttcgg taaattggta ttcccccttt     300
tatgtgattg gtcattgatc attgttagtg gccagacatt tgaactcccg tttttttgtc     360
tataagaatt cggaaacata tagtatcctt tgaaaacgga gaaacaaata acaatgtgga     420
caaactagat ataatttcaa cacaagacta tgggaatgat tttacccact aattataatc     480
cgatcacaag gtttcaacga actagttttc cagatatcaa ccaaatttac tttggaatta     540
aactaactta aaactaattg gttgttcgta aatggtgctt ttttttttg cggatgttag      600
taaagggttt tatgtatttt atattattag ttatctgttt tcagtgttat gttgtctcat     660
ccataaagtt tatatgttttt ttctttgctc tataacttat atatatat gagtttacag       720
ttatatttat acatttcaga tacttgatcg gcattttttt tggtaaaaaa tatatgcatg     780
aaaaactcaa gtgtttcttt tttaaggaat ttttaaatgg tgattatatg aatataatca     840
tatgtatatc cgtatatata tgtagccaga tagttaatta tttgggggat atttgaatta     900
ttaatgttat aatattcttt cttttgactc gtctggttaa attaaagaac aaaaaaaaca     960
catactttta ctgttttaaa aggttaaatt aacataattt attgattaca agtgtcaagt    1020
ccatgacatt gcatgtaggt tcgagacttc agagataacg gaagagatcg ataattgtga    1080
tcgtaacatc cagatatgta tgtttaattt tcatttagat gtggatcaga aagataagt     1140
caaactgtct tcataattta agacaaacctc ttttaatatt ttcccaaaac atgttttatg    1200
taactacttt gcttatgtga ttgcctgagg atactattat tctctgtctt tattctcttc    1260
acaccacatt taaatagttt aagagcatag aaattaatta ttttcaaaaa ggtgattata    1320
tgcatgcaaa atagcacacc atttatgttt atattttcaa attatttaat acatttcaat    1380
atttcataag tgtgattttt tttttttttg tcaatttcat aagtgtgatt tgtcatttgt    1440
attaaacaat tgtatcgcgc agtacaaata aacagtggga gaggtgaaaa tgcagttata    1500
aaactgtcca ataatttact aacacattta aatatctaaa aagagtgttt caaaaaaat     1560
tcttttgaaa taagaaaagt gatagatatt tttacgcttt cgtctgaaaa taaaacaata    1620
atagtttatt agaaaaatgt tatcaccgaa aattattcta gtgccactcg ctcggatcga    1680
aattcgaaag ttatattctt tctctttacc taatataaaa atcacaagaa aaatcaatcc    1740
gaatatatct atcaacatag tatatgccct tacatattgt ttctgacttt tctctatccg    1800
aatttctcgc ttcatggttt tttttaaca tattctcatt taattttcat tactattata    1860
taactaaaag atggaaataa aataaagtgt ctttgagaat cgaacgtcca tatcagtaag    1920
atagtttgtg tgaaggtaaa atctaaaaga tttaagttcc aaaaacagaa aataatatat    1980
tacgctaaaa aagaagaaaa taattaaata caaaacagaa aaaataata tacgacagac    2040
acgtgtcacg aagataccct acgctataga cacagctctg ttttctcttt tctatgcctc    2100
```

-continued

```
aaggctctct taacttcact gtctcctctt cggataatcc tatccttctc ttcctataaa    2160
tacctctcca ctcttcctct tcctccacca ctacaaccac cgcaacaacc accaaaaacc    2220
ctctcaaaga aatttctttt ttttcttact ttcttggttt gtcaaat                  2267
```

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8

```
tatgaccatg attacgccaa gcttaagaag ttgattttgg ac                         42
```

<210> SEQ ID NO 9
<211> LENGTH: 42
<212> TYPE: DNA
<213> ORGANISM: Artificial Sequence
<220> FEATURE:
<223> OTHER INFORMATION: primer

<400> SEQUENCE: 9

```
acccggggat cctctagagt cgaccgtagc ttttagaaag aa                         42
```

<210> SEQ ID NO 10
<211> LENGTH: 42
<212> TYPE: DNA
<213> ORGANISM: Artificial Sequence
<220> FEATURE:
<223> OTHER INFORMATION: primer

<400> SEQUENCE: 10

```
tatgaccatg attacgccaa gcttacgcaa actaactaca ac                         42
```

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11

```
acccggggat cctctagagt cgacatttga caaaccaaga aa                         42
```

<210> SEQ ID NO 12
<211> LENGTH: 40
<212> TYPE: DNA
<213> ORGANISM: Artificial Sequence
<220> FEATURE:
<223> OTHER INFORMATION: primer

<400> SEQUENCE: 12

```
agcttggcgc gccttaatta aactagtctc gaggtcgact                            40
```

<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13

```
ctagagtcga cctcgagact agtttaatta aggcgcgcca                            40
```

<210> SEQ ID NO 14
<211> LENGTH: 47
<212> TYPE: DNA
<213> ORGANISM: Artificial Sequence
<220> FEATURE:
<223> OTHER INFORMATION: primer

<400> SEQUENCE: 14
aattactatt tacaattaca gtcgacatgg gacatttctc ttccatg        47

<210> SEQ ID NO 15
<211> LENGTH: 43
<212> TYPE: DNA
<213> ORGANISM: Artificial Sequence
<220> FEATURE:
<223> OTHER INFORMATION: primer

<400> SEQUENCE: 15
cgggcggccg ctttacttgt acactataga gatggcgacg acg            43

<210> SEQ ID NO 16
<211> LENGTH: 62
<212> TYPE: DNA
<213> ORGANISM: Artificial Sequence
<220> FEATURE:
<223> OTHER INFORMATION: primer

<400> SEQUENCE: 16
aattactatt tacaattaca gtcgacatga agtcttttg tgataatgat gataataatc    60
at                                                                  62

<210> SEQ ID NO 17
<211> LENGTH: 48
<212> TYPE: DNA
<213> ORGANISM: Artificial Sequence
<220> FEATURE:
<223> OTHER INFORMATION: primer

<400> SEQUENCE: 17
agccgggcgg ccgctttact tgtacatcaa gaatcagccc aagcagcg       48

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
ttctttctaa aagctacggt cgacatggga catttctctt cc              42

<210> SEQ ID NO 19
<211> LENGTH: 42
<212> TYPE: DNA
<213> ORGANISM: Artificial Sequence
<220> FEATURE:
<223> OTHER INFORMATION: primer

<400> SEQUENCE: 19
gaacgatcgg ggaaattcga gctcctatag agatggcgac ga              42

<210> SEQ ID NO 20
<211> LENGTH: 42
<212> TYPE: DNA
<213> ORGANISM: Artificial Sequence

```
<220> FEATURE:
<223> OTHER INFORMATION: primer

<400> SEQUENCE: 20
ttctttctaa aagctacggt cgacatgaag tcttttgtg at                    42

<210> SEQ ID NO 21
<211> LENGTH: 42
<212> TYPE: DNA
<213> ORGANISM: Artificial Sequence
<220> FEATURE:
<223> OTHER INFORMATION: primer

<400> SEQUENCE: 21
gaacgatcgg ggaaattcga gctctcaaga atcagcccaa gc                   42

<210> SEQ ID NO 22
<211> LENGTH: 42
<212> TYPE: DNA
<213> ORGANISM: Artificial Sequence
<220> FEATURE:
<223> OTHER INFORMATION: primer

<400> SEQUENCE: 22
tttcttggtt tgtcaaatgt cgacatggga catttctctt cc                   42

<210> SEQ ID NO 23
<211> LENGTH: 42
<212> TYPE: DNA
<213> ORGANISM: Artificial Sequence
<220> FEATURE:
<223> OTHER INFORMATION: primer

<400> SEQUENCE: 23
gaacgatcgg ggaaattcga gctcctatag agatggcgac ga                   42

<210> SEQ ID NO 24
<211> LENGTH: 42
<212> TYPE: DNA
<213> ORGANISM: Artificial Sequence
<220> FEATURE:
<223> OTHER INFORMATION: primer

<400> SEQUENCE: 24
tttcttggtt tgtcaaatgt cgacatgaag tcttttgtg at                    42

<210> SEQ ID NO 25
<211> LENGTH: 42
<212> TYPE: DNA
<213> ORGANISM: Artificial Sequence
<220> FEATURE:
<223> OTHER INFORMATION: primer

<400> SEQUENCE: 25
gaacgatcgg ggaaattcga gctctcaaga atcagcccaa gc                   42
```

PLANT SUITABLE FOR INCREASING PRODUCTION OF PHLOEM TISSUE AND USE OF SAME

CROSS REFERENCE TO RELATED APPLICATIONS

This application is related to Japanese Patent Application No. 2013-187742 filed on Sep. 10, 2013 and claims priority to the Japanese application entire contents of which are incorporated by reference herein.

TECHNICAL FIELD

This description relates to a plant suitable for increasing production of phloem tissue and use of same.

DESCRIPTION OF RELATED ART

Increasing the amount of plant biomass is important for avoiding food supply crises and also important from an industrial point of view.

Numerous attempts have previously been made to increase plant production. For example, a technology has been disclosed for increasing the production of plant biomass by overexpression of protein phosphatase 2C (PP2C) under the control of cauliflower mosaic virus 35S (CaMV35S) promoter (WO 2009/113684). In addition, leaves, flower organs and the like have been disclosed to be enlarged by overexpression of ARGOS for which expression is induced by auxins (Yuxin Hu et al., Plant Cell 2003, 15(9): 1951-1961). Moreover, plant growth and cell growth have been disclosed to be regulated by regulating the activity of AINTEGUMENTA (ANT) (Japanese Translation of PCT Application No. 2002-534078, Mizukami, Y., Fischer, R. L., Proc. Natl. Acad. Sci., USA 97, 942-947).

BRIEF SUMMARY OF INVENTION

Plant phloem tissue is considered to be more important than other plant tissue from the viewpoint of serving as a raw material of materials such as fibers or rubber as well as biofuels. In addition, in fibrous plants in which fibers are obtained from phloem tissue, in order to increase production of high-quality fibers, it is required to increase the ratio of phloem tissue to unwanted portions such as the xylem or pith, namely increase the phloem ratio.

However, CaMV35S promoter is extremely seasonally- and tissue-non-specific. Consequently, although production of biomass was increased, it was difficult to efficiently obtain phloem tissue. In addition, the use of a seasonally- and tissue-non-specific promoter results in the risk of inducing growth disorders and metabolic abnormalities due to the overexpression thereof depending on the type of structural gene.

The present description provides a plant suitable for acquisition of phloem tissue and the use thereof.

The inventors of the present invention searched for various promoters in order to obtain a plant that demonstrated an increased phloem ratio suitable for acquisition of phloem tissue. As a result, it was found that phloem tissue can be selectively increased as a result of expressing a gene encoding a protein that promotes cell growth under the control of a promoter specifically expressed in vascular cambium. Vascular cambium is a tissue that is able to differentiate into phloem tissue. On the basis of this finding, the following means are provided according to the disclosure of the present description.

(1) A plant having plant cells retaining a vascular cambium-specific promoter specifically expressed in the vascular cambium of a plant and/or a phloem cell-specific promoter specifically expressed in the phloem cells of the plant, and a cell growth-promoting gene encoding a protein that promotes cell growth under the control of the vascular cambium-specific promoter or the phloem tissue-specific promoter.

(2) The plant according to (1), wherein the cell growth-promoting gene is a first cell growth-promoting gene that promotes cell growth under the control of the vascular cambium-specific promoter,
the plant further comprising a second cell growth-promoting gene that promotes cell growth under the control of the phloem tissue-specific promoter.

(3) The plant according to claim (1) or (2), wherein phloem tissue of the plant is specifically increased.

(4) The plant according to any one of (1)-(3), wherein the promoter is selected from the group consisting of a promoter functionally equivalent to tracheary element differentiation inhibitory factor (TDIF) receptor (TDR) promoter, a promoter that is functionally equivalent to sucrose transport protein SUC2 promoter, a promoter that is functionally equivalent to phloem intercalated with xylem (PXY) promoter, a promoter that is functionally equivalent to Dof-type zinc finger domain-containing protein (Dof5.6) promoter, and a promoter that is functionally equivalent to high cambial activity 2 (HCA2) promoter.

(5) The plant according to any one of (1)-(4), wherein the protein is a protein having three common sequences composed of the amino acid sequences represented by SEQ ID NO: 1 to 3 in this order starting from the N-terminal side.

(6) The plant according to any one of (1)-(5), wherein the protein is a protein having 95% or more identity with the amino acid sequence represented by SEQ ID NO: 5.

(7) The plant according to any one of (1)-(6), wherein an amount of phloem tissue of the plant is increased by 2.0 times or more in comparison with a wild strain.

(8) The plant according to any one of (1)-(7), which is a dicotyledon.

(9) The plant according to any one of (1)-(8), which is a plant of the Brassicaceae family.

(10) The plant according to any one of (1)-(9), which is a monocotyledon.

(11) The plant according to any one of (1)-(10), which is a plant of the Gramineae family.

(12) The plant according to any one of (1)-(11), which is a plant of the Malvaceae family.

(13) A method for producing the plant according to any one of (1)-(12).

(14) A method for increasing production of phloem tissue of a plant, comprising a step of cultivating the plant according to any one of (1)-(12).

(15) The method for increasing production according to (14), wherein a ratio of the weight of the phloem tissue is increased with respect to the total weight of the plant.

DETAILED DESCRIPTION OF INVENTION

Figure 1:
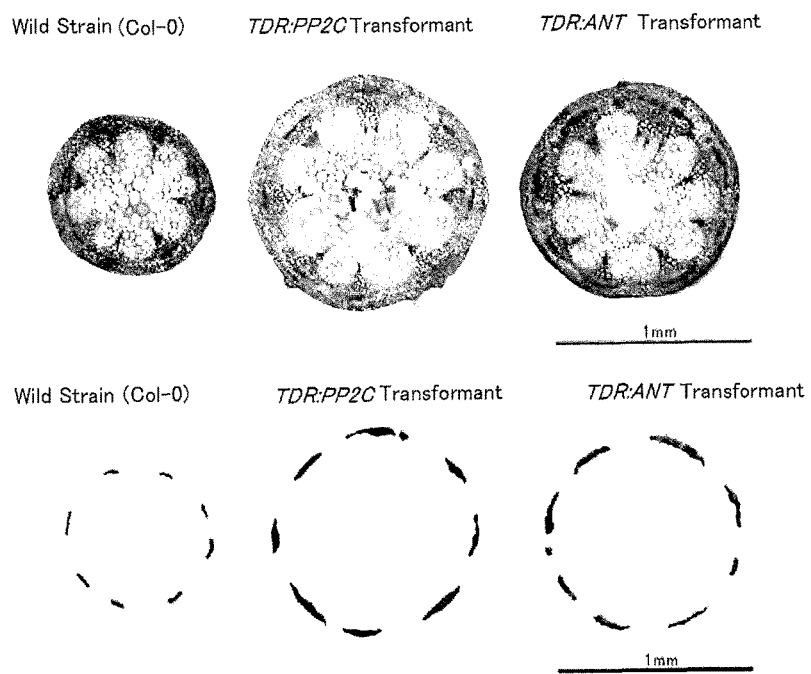
FIG. 1 shows transverse cross-sections of the stems of wild strain *Arabidopsis thaliana* (Col-0), stain TDR:PP2C and stain TDR:ANT.

The present description relates to a plant suitable for increasing production of phloem tissue and the use thereof. The present description is based on the inventors of the present invention having succeeded in introducing into a plant a cell growth-promoting gene encoding a protein that promotes cell growth under the control of a promoter specifically expressed in plant vascular cambium or phloem cells and the cultivation of that plant, and on this causing a specific increase in phloem tissue. The term "increase in phloem tissue" herein includes, but not limited to, enlargement or expansion of the phloem tissue, growth of the phloem tissue, or proliferation or multiplication of the phloem tissue, or any combination thereof.

The following relates to disclosure of the present description and provides a detailed explanation of a plant, plant production method and method for increasing production of phloem tissue in that order.

Furthermore, in the present disclosure, "phloem tissue" can be provided with sieve tubes, companion cells, phloem fiber and phloem parenchyma. Phloem tissue is tissue for transporting nutrients such as photosynthesis products. Phloem tissue forms vascular bundles together with xylem tissue, vascular cambium and the like.

In addition, in the present disclosure, "vascular cambium" can be provided with fusiform initial cells and ray initial cells. Fusiform initial cells and ray initial cells undergo cell division in the vascular cambium. In addition, the vascular cambium is provided with secondary phloem. Secondary phloem is composed of sieve tubes, companion cells, phloem fiber and phloem parenchyma in the same manner as phloem. Namely, the phloem tissue of the present description includes secondary phloem.

In addition, in the present disclosure, "phloem cells" refers to cells that form phloem tissue. Phloem cells can include companion cells, phloem parenchymal cells and the like.

(Plant)

The plant disclosed in the present description is able to retain a vascular cambium-specific promoter, specifically expressed in the vascular cambium of a plant, or a phloem cell-specific promoter, specifically expressed in the phloem cells of the plant, and a cell growth-promoting gene encoding a protein that promotes cell growth under the control of the above-mentioned vascular cambium-specific promoter or phloem cell-specific promoter.

(Vascular Cambium-Specific Promoters and Phloem Tissue-Specific Promoters)

Vascular cambium-specific promoters are specifically expressed in the vascular cambium of a plant, while phloem cell-specific promoters are specifically expressed in phloem cells. Vascular cambium-specific promoters and phloem cell-specific promoters are able to increase phloem tissue by controlling expression of a cell growth-promoting gene. In the present description, the phrase "specifically expressed" in a specific tissue or cells is not limited to the expression of a gene in that tissue or cells alone, but also includes expression that is comparatively strong in that cell or tissue and comparatively weak in other tissue.

(Vascular Cambium-Specific Promoters)

(TDR Promoter)

TDR promoter is one type of vascular cambium-specific promoter. TDR promoter is a promoter that controls expression of a gene encoding TDR, which is a receptor of tracheary element differentiation inhibitory factor (TDIF). Receptor TDR, localized in the vascular procambium or vascular bundle stem cells present in the vascular cambium, binds with TDIF produced in phloem tissue and is secreted outside the cells, transmits signals from the TDIF to inside the cells and inhibits differentiation from vascular bundle stem cells into xylem by binding with receptor TDR localized in vascular bundle stem cells to promote division of vascular bundle stem cells. TDR promoter can have a base sequence represented by SEQ ID NO: 6, for example, and may be a portion thereof provided it has promoter activity that is functionally equivalent to that of DNA having the base sequence represented by SEQ ID NO: 6. The base sequence represented by SEQ ID NO: 6 is that of a TDR promoter of *Arabidopsis thaliana*.

The vascular cambium-specific promoter is not required to be identical to TDR promoter, and may also be a promoter of an orthologous gene and the like that is functionally equivalent to TDR gene. Here, "functionally equivalent" refers to a promoter of a gene encoding a protein specifically expressed in the vascular cambium.

Furthermore, a functionally equivalent promoter refers to a protein encoded by a gene controlled by that promoter typically having a peptide chain composed of an amino acid sequence having identity with the amino acid sequence of TDR of *Arabidopsis thaliana* of at least 60% or more, preferably 70% or more, more preferably 80% or more, even more preferably 90% or more, still more preferably 91% or more, yet even more preferably 92% or more, yet even more preferably 93% or more, yet even more preferably 94% or more, yet even more preferably 95% or more, yet even more preferably 96% or more, yet even more preferably 97% or more, yet even more preferably 98% or more and most preferably 99% or more. In addition, a protein encoded by such a gene typically has a peptide chain composed of an amino acid sequence having identity with the base sequence of TDR gene of at least 70% or more, preferably 80% or more, more preferably 90% or more, even more preferably 91% or more, still more preferably 92% or more, yet even more preferably 93% or more, yet even more preferably 94% or more, yet even more preferably 95% or more, yet even more preferably 96% or more, yet even more preferably 97% or more, yet even more preferably 98% or more and most preferably 99% or more.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

Examples of proteins having a fixed level of identity or more with the amino acid sequence of *Arabidopsis thaliana* TDR include hypothetical protein ARALDRAFT496307 (*Arabidopsis lyrata* subsp. *lyrata*, accession no.: XP_002866438.1), predicted protein *Populus trichocarpa* (accession no: XP_002303493.1), predicted leucine-rich repeat receptor-like protein kinase TDR-like (*Cucumis sativus*, accession no.: XP_004166710.1), predicted leucine-rich repeat receptor-like protein kinase TDR-like (*Cucumis sativus*, accession no.: XP_004146946.1), predicted leucine-rich repeat receptor-like protein kinase TDR-like (*Vitis vinifera*, accession no: XP 002268598.2), predicted leucine-rich repeat receptor-like protein kinase TDR-like (*Glycine max*, accession no.: XP_003539668.1), predicted leucine-rich repeat receptor-like protein kinase TDR-like (*Solanum lycopersicum*, accession no.: XP_004235172.1), predicted leucine-rich repeat receptor-like protein kinase TDR-like (*Glycine max*, accession no.: XP_003533511.1), predicted leucine-rich repeat receptor-like protein kinease TDR-like (*Cicer arietinum*, accession no: XP_004514509.1), predicted leucine-rich repeat receptor-like protein kinase TDR-like (*Fragaria vesca* subsp. *vesca*, accession no.: XP_004307799.1), predicted leucine-rich repeat receptor-like protein kinase TDR-like (*Solanum lycopersicum*, accession no.: XP_004240244.1), predicted leucine-rich repeat receptor-like protein kinase TDR-like (*Setaria italica*, accession no.: XP_004972862.1), and predicted leucine-rich repeat receptor-like protein kinase TDR-like (*Vitis vinifera*, accession no.: XP_002264530.2).

In addition, coding regions having a fixed level of identity or more with the base sequence encoding *Arabidopsis thaliana* TDR gene include *Arabidopsis lyrata* subsp. *lyrata* hypothetical protein, mRNA (accession no.: XM_002866392.1), *Arabidopsis lyrata* subsp, *lyrata* hypothetical protein, mRNA (accession no.: XM_002891404.1), *Brassica rapa* subsp. *pekinensis* clone KBrH005L20, complete sequence (accession no.: AC232542.1), predicted *Cicer arietinum* leucine-rich repeat receptor-like serine/threonine-protein kinase At1g17230-like (LOC101489235), transcript variant X2, mRNA (accession no.: XM_004488655.1), and predicted *Cicer arietinum* leucine-rich repeat receptor-like serine/threonine-protein kinase At1g17230-like (LOC101489235), transcript variant X1, mRNA (accession no.: XM_004488654.1). Coding regions able to be used can be suitably selected therefrom by a person skilled in the art.

(Phloem Cell-Specific Promoters)
(SUC2 Promoter)

SUC2 promoter is a promoter that controls expression of a gene encoding sucrose transport protein SUC2. SUC2 is a symporter that transports sucrose together with protons. Sucrose is broken down into glucose and fructose and is used as a material and energy source for starch synthesis. In addition, SUC2 is also able to transport maltose, albutin, salicin, α-phenylglucoside, β-phenylglucoside, α-paranitrophenylglucoside, β-paranitrophenylglucoside, paranitrophenyl-β-thioglucoside and biotin. Sucrose in phloem tissue is accumulated in tissue serving as a supply source such as leaves, and is transported to tissue serving as an absorption source such as roots or flowers. SUC2 promoter can have the base sequence represented by SEQ ID NO: 7, for example, and may be a portion thereof provided it has promoter activity that is functionally equivalent to DNA having the base sequence represented by SEQ ID NO: 7. *Arabidopsis thaliana* SUC2 (SUT1, AtSUC2) gene of the base sequence represented by SEQ ID NO: 7 is a sucrose transport protein classified as type 1 in FIG. 1 of Front Plant Sci., 2012, 3:22. Furthermore, SUC2 promoter is expressed in phloem cells.

The phloem cell-specific promoter is not required to be identical to SUC2 promoter, and may also be a promoter of an orthologous gene and the like functionally equivalent to SUC2 promoter. Here, "functionally equivalent" refers to a promoter of a gene encoding a protein specifically expressed phloem cells.

Furthermore, a protein encoded by a gene controlled by such a promoter typically has a peptide chain composed of an amino acid sequence having identity with the amino acid sequence of SUC2 of *Arabidopsis thaliana* of at least 60% or more, preferably 70% or more, more preferably 80% or more, even more preferably 90% or more, still more preferably 91% or more, yet even more preferably 92% or more, yet even more preferably 93% or more, yet even preferably, yet even more preferably 95% or more, yet even more preferably 96% or more, yet even more preferably 97% or more, yet even more preferably 98% or more and most preferably 99% or more. In addition, a protein encoded by such a gene typically has a peptide chain composed of an amino acid sequence having identity with the base sequence of SUC2 gene of at least 70% or more, preferably 80% or more, more preferably 90% or more, even more preferably 91% or more, still more preferably 92% or more, yet even more preferably 93% or more, yet even more preferably 94% or more, yet even more preferably 95% or more, yet even more preferably 96% or more, yet even more preferably 97% or more, yet even more preferably 98% or more and most preferably 99% or more.

Examples of proteins having a fixed level of identity or more with the amino acid sequence of SUC of *Arabidopsis thaliana* include sucrose-protein symporter 2 (*Arabidopsis lyrata* subsp. *lyrata*, accession no.: XP_002893246.1), hypothetical protein ARALYDRAFT 476315 (*Arabidopsis lyrata* subsp. *lyrata*, accession no.: XP_002887397.1), hypothetical protein ARALYDRAFT 497263 (*Arabidopsis lyrata* subsp. *lyrata*, accession no.: XP_002862880.1), sucrose-proton symporter 1 (*Arabidopsis lyrata* subsp. *lyrata*, accession no.: XP_002887396.1), sucrose transport protein, putative (*Ricinus communis*, accession no.: XP_002526849.1), sucrose-proton symporter 6 (*Arabidopsis lyrata* subsp. *lyrata*, accession no.: XP_002871200.1), predicted sucrose transport protein-like (*Cicer arietinum*, accession no.: XP_004496382.1), hypothetical protein ARALYDRAFT 911231 (*Arabidopsis lyrata* subsp, *lyrata*, accession no.: XP_002874582.1), predicted protein (*Arabidopsis lyrata subsp. lyrata, accession no.: XP_002887046.1), sucrose proton symporter (*Populus trichocarpa*, accession no.: XP_002326003.1), sucrose proton symporter (*Populus trichocarpa*, accession no.: XP_002327228.1), sucrose transporter (*Glycine max*, accession no.: NP 001236298.1), predicted sucrose protein SUC2 (*Solanum lycopersicum*, accession no.: XP\004250368.1), predicted sucrose transport protein SUC2-like (*Fragaria vesca* subsp. *vesca*, accession no: XP_004290438.1), predicted sucrose transport protein SUC5-like (*Cicer arietinum*, accession no.: XP_004515134.1), sucrose proton symporter (*Populus trichocarpa*, accession no.: XP_002333323.1), predicted sucrose transport protein SUC2-like (*Fragaria vesca* subsp. *vesca*, accession no.: XP_004291895.1), sucrose transporter-like (*Vitis vinifera*, accession no.: NP_001268070.1), predicted sucrose transport protein SUC2 (*Vitis vinifera*, accession no.: XP_002266122.1), predicted sucrose transport protein SUC2-like (*Cicer arietinum*, accession no.: XP_004515590.1), predicted sucrose transport protein SUC2-like (*Fragaria vesca* subsp. *vesca*, accession no.: XP_004289897.1), sucrose transport protein (*Medicago truncatula*, accession no.: XP_003610412.1), predicted sucrose transport protein SUC2-like (*Glycine max*, accession no.: XP_003548077.1), predicted sucrose transport protein SUC2-like (*Glycine max*, accession no.: XP_003548952.1), predicted sucrose transport protein SUC2-like (*Fragaria vesca* subsp. *vesca*, accession no.: XP_004291896.1), predicted sucrose transport protein SUC2-like (*Glycine max*, accession no.: XP_003518348.1), predicted sucrose transport protein SUC2-like (*Cucumis sativus*, accession no.: XP_003548078.1), predicted sucrose transport protein SUC2-like (*Cucumis sativus*, accession no.: XP_004138920.1), predicted sucrose transport protein SUC2-like (*Cucumis sativus*, accession no.: XP-004159998.1), predicted sucrose transport protein SUC2-like (*Fragaria vesca* subsp. *vesca*, accession no.: XP_004298889.1), predicted sucrose transport protein SUC2-like (*Glycine max*, accession no.: XP_003548076.1), predicted sucrose transport protein SUC2-like (*Glycine max*, accession no.: XP_003518345.1), hypothetical protein ARALYDRAFT_319456 (*Arabidopsis lyrata* subsp. *lyrata*, accession no.: XP_002885931.1), Os02g0827200 (*Oryza sativa Japonica* Group, accession no.: NP_001048591.1), hypothetical protein SORBIDRAFT_04 g038030 (*Sorghum bicolor*, accession no.: XP_002453083.1), and predicted sucrose transport protein SUT1-like (*Brachypodium distachyon*, accession no.: XP_003558709.1). In addition, another example known to be localized in vascular bundle phloem companion cells of *Oryza sativa* is Os03g0170900 (*Oryza sativa Japonica* Group, accession no.: NP_001049111.1) (Chi-aki, M. et al., (2000), Plant Physiology, 124, 85-93).

In addition, examples of coding regions having a fixed level of identity or more with a base sequence encoding SUC2 gene of *Arabidopsis thaliana* include *Arabidopsis lyrata* subsp. *lyrata* sucrose-proton symporter 2 (SUC2), mRNA (accession no.: XM_002893200.1), *Brassica oleracea* sucrose transporter SUC2 (SUC2) mRNA, complete cds (accession no.: AY065840.1), *Brassica napus* sucrose transporter (SUT) mRNA, compete cds (accession no.: EU570076.1), *Arabidopsis lyrata* subsp. *lyrata* sucrose-proton symporter 1 (SUC1), mRNA (accession no.: XM_002887350.1), *Arabidopsis lyrata* subsp. *lyrata* hypothetical protein, mRNA (accession no.: XM_002887351.1) and *Arabidopsis lyrata* subsp. *lyrata* hypothetical protein, mRNA (accession no.: XM_002862834.1). Coding regions able to be used can be suitably selected therefrom by a person skilled in the art.

Promoters other than TDR promoters and SUC2 promoters that are specifically expressed in vascular cambium or phloem cells can also be used. Examples of such promoters include phloem intercalated with xylem (PXY) promoter, Dof-type zinc finger domain-containing protein (Dof5.6) promoter and high cambial activity 2 (HCA2) promoter. All of these base sequences can be acquired from the NCBI database.

(Cell Growth-Promoting Gene)

A cell growth-promoting gene is a gene encoding a protein that promotes cell growth. Examples of such genes include protein phosphatase 2C (PP2C) gene, AINTEGUMENTA (ANT) gene, Hercules 1 (HRC1) gene, NAM/CUC-like Protein 1 (NAC1) gene, ARGOS gene, DWF4 gene, gibberellin 20-oxidase 1 (GA20OX1) gene, cyclin B1-1 (CYB1-1) gene and cyclin D2-1 (CYD2-1) gene. In addition, other examples include E2Fa gene and/or dimerization partner (DPa) gene. All of these base sequences can be acquired from the NCBI database.

(PP2C (Protein Phosphatase 2C) Gene)

The protein phosphatase 2C gene to be over-expressed in a plant encodes protein phosphatase 2C that has 3 consensus sequences comprising the amino acid sequences shown in SEQ ID NOS: 1-3 in such order from the N-terminal side. In addition, a gene group classified as Group E as in FIG. 1 of Topographic cladogram (on page 237 of Reference: TRENDS in Plant Science Vol. 9 No. 5 May 2004 pages 236-243) encodes protein phosphatase 2C having 3 consensus sequences comprising the amino acid sequences shown in SEQ ID NOS: 1-3 in such order from the N-terminal side. In addition, the reference predicts the presence of 76 protein phosphatase 2C genes in *Arabidopsis thaliana* and discloses the results of producing a phylogenetic tree of these genes using T-Coffee software (reference; Notredame, C. et al. 2000 T-Coffee: a novel method for fast and accurate multiple sequence alignment. J. Mol. Biol. 302, 205-247) as in FIG. 1. In this phylogenetic tree, protein phosphatase 2C genes classified as members of Group E encode protein phosphatase 2C that has 3 consensus sequences comprising the amino acid sequences shown in SEQ ID NOS: 1-3 in such order from the N-terminal side. The 3 consensus sequences comprising the amino acid sequences shown in SEQ ID NOS: 1-3 are characteristic sequences in Group E in the above-mentioned classification and serve as a basis for clear differentiation from other groups.

Group E in the above classification includes protein phosphatase 2C genes specified by *Arabidopsis thaliana*-derived At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270. FIG. 1 shows the results of alignment analysis using a CLUSTAL W (1.83) multiple sequence alignment program (which can be used with the DDBJ of the National Institute of Genetics for the amino acid sequences encoded by these *Arabidopsis thaliana*-derived protein phosphatase 2C genes, At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270 (with the amino acid (sequence) substitution matrix used herein being a default matrix known as BLOSUM (Blocks of Amino Acid Substitution Matrix)). As shown in FIG. 1, these protein phosphatase 2C genes classified as members of Group E have consensus sequences characteristic in the regions denoted as I to III. These regions denoted as I to III are subjected with a rice-derived protein phosphatase 2C gene (described later) to alignment analysis, so that the 3 consensus sequences comprising the amino acid sequences shown in SEQ ID NOS: 1-3 can be defined.

Herein, in the amino acid sequence shown in SEQ ID NO: 1, which is an amino acid residue denoted as "Xaa," may be any amino acid, and it is not limited to any particular amino acid. However, the 1st amino acid residue from the N-terminal side in the amino acid sequence shown in SEQ ID NO: 1 is preferably leucine (three character code: Leu and single character code: L; the same applies to the following) or phenylalanine (Phe, F). The 4th amino acid residue from the N-terminal side in the amino acid sequence shown in SEQ ID NO: 1 is preferably valine (Val, V), isoleucine (Ile, I), or methionine (Met, M). The 16th amino acid residue from the N-terminal side in the amino acid sequence shown in SEQ ID NO: 1 is preferably serine (Ser, S) or alanine (Ala, A). The 17th amino acid residue from the N-terminal side in the amino acid sequence shown in SEQ ID NO: 1 is preferably lysine (Lys, K), arginine (Arg, R), glutamine (Gln, Q), or asparagine (Asn, N). More specifically, a consensus sequence comprising the amino acid sequence shown in SEQ ID NO: 1 is preferably (L/F)XG(V/I/M)FDGH-GXXGXXX(S/A)(K/R/Q/N)XV. In such amino acid sequence, pluralities of amino acids in parentheses represent possible variations of amino acid residues at the relevant positions. Also, in the following amino acid sequences, "X" means that any amino acid residue may be present at the relevant position.

Also, such a consensus sequence may be a sequence containing the following 3 amino acid residues on the N-terminal side of Region I in FIG. 1: (D/E/N)XX.

Here, in the amino acid sequence shown in SEQ ID NO: 2, an amino acid residue denoted as "Xaa," may be any amino acid, and it is not limited to any particular amino acid. However, the 5th amino acid residue from the N-terminal side in the amino acid sequence shown in SEQ ID NO: 2 is preferably glycine (Gly, G), alanine (Ala, A), or serine (Ser, S). The 6th amino acid residue from the N-terminal side in the amino acid sequence shown in SEQ ID NO: 2 is preferably valine (Val, V), leucine (Leu, L), or isoleucine (Ile, I). The 9th amino acid residue from the N-terminal side in the amino acid sequence shown in SEQ ID NO: 2 is preferably isoleucine (Ile, I), valine (Val, V), phenylalanine (Phe, F), methionine (Met, M), or leucine (Leu, L). The 12th amino acid residue from the N-terminal side in the amino acid sequence shown in SEQ ID NO: 2 is preferably glycine (Gly, G) or alanine (Ala, A). The 15th amino acid residue from the N-terminal side in the amino acid sequence shown in SEQ ID NO: 2 is preferably leucine (Leu, L), valine (Val, V), or isoleucine (Ile, I). The 17th amino acid residue from the N-terminal side in the amino acid sequence shown in SEQ ID NO: 2 is preferably isoleucine (Ile, I), valine (Val, V), or methionine (Met, M). The 18th amino acid residue from the N-terminal side in the amino acid sequence shown in SEQ ID NO: 2 is preferably glycine (Gly, G) or alanine (Ala, A). The 22nd amino acid residue from the N-terminal side in the amino acid sequence shown in SEQ ID NO: 2 is preferably aspartic acid (Asp, D) or histidine (His, H). The 26th amino acid residue from the N-terminal side in the amino acid sequence shown in SEQ ID NO: 2 is preferably valine (Val, V) or isoleucine (Ile, I). The 27th amino acid residue from the N-terminal side in the amino acid sequence shown in SEQ ID NO: 2 is preferably leucine (Leu, L), methionine (Met, M), or isoleucine (Ile, I). More specifically, a consensus sequence comprising the amino acid sequence shown in SEQ ID NO: 2 is preferably SGXT(G/A/S)(V/L/I)XX(I/V/F/M/L)XX(G/A)XX(L/V/I)X(I/V/M)(A/G)NXG(D/H)SRA(V/I)(L/M/I). In such amino acid sequence, pluralities of amino acids in parentheses represent possible variations of amino acid residues at the relevant positions. Also, in the following amino acid sequences, "X" means that any amino acid residue may be present at the relevant position.

Here, the amino acid sequence shown in SEQ ID NO: 3, an amino acid residue denoted as "Xaa," may be any amino acid, and it is not limited to any particular amino acid. However, the 4th amino acid residue from the N-terminal side in the amino acid sequence shown in SEQ ID NO: 3 is preferably methionine (Met, M), valine (Val, V), or phenylalanine (Phe, F). The 5th amino acid residue from the N-terminal side in the amino acid sequence shown in SEQ ID NO: 3 is preferably serine (Ser, S), alanine (Ala, A), or threonine (Thr, T). The 7th amino acid residue from the N-terminal side in the amino acid sequence shown in SEQ ID NO: 3 is preferably alanine (Ala, A) or serine (Ser, S). The 8th amino acid residue from the N-terminal side in the amino acid sequence shown in SEQ ID NO: 3 is preferably phenylalanine (Phe, F), isoleucine (Ile, I), or valine (Val, V). The 14th amino acid residue from the N-terminal side in the amino acid sequence shown in SEQ ID NO: 3 is preferably lysine (Lys, K) or glutamic acid (Glu, E). The 18th amino acid residue from the N-terminal side in the amino acid sequence shown in SEQ ID NO: 3 is preferably valine (Val, V) or leucine (Leu, L). The 19th amino acid residue from the N-terminal side in the amino acid sequence shown in SEQ ID NO: 3 is preferably isoleucine (Ile, I) or valine (Val, V). The 23rd amino acid residue from the N-terminal side in the amino acid sequence shown in SEQ ID NO: 3 is preferably glutamic acid (Glu, E), glutamine (Gln, Q), or aspartic acid (Asp, D). The 24th amino acid residue from the N-terminal side in the amino acid sequence shown in SEQ ID NO: 3 is preferably isoleucine (Ile, I), valine (Val, V), or phenylalanine (Phe, F). The 29th amino acid residue from the N-terminal side in the amino acid sequence shown in SEQ ID NO: 3 is preferably isoleucine (Ile, I), leucine (Leu, L), or valine (Val, V). The 30th amino acid residue from the N-terminal side in the amino acid sequence shown in SEQ ID NO: 3 is preferably serine (Ser, S), threonine (Thr, T), or asparagine (Asn, N). The 33rd amino acid residue from the N-terminal side in the amino acid sequence shown in SEQ ID NO: 3 is preferably aspartic acid (Asp, D), asparagine (Asn, N), or histidine (His, H). The 35th amino acid residue from the N-terminal side in the amino acid sequence shown in SEQ ID NO: 3 is preferably phenylalanine (Phe, F) or tyrosine (Tyr, Y). The 36th amino acid residue from the N-terminal side in the amino acid sequence shown in SEQ ID NO: 3 is preferably leucine (Leu, L), isoleucine (Ile, I), valine (Val, V), phenylalanine (Phe, F), or methionine (Met, M). The 37th amino acid residue from the N-terminal side in the amino acid sequence shown in SEQ ID NO: 3 is preferably valine (Val, V), leucine (Leu, L), or isoleucine (Ile, I). The 38th amino acid residue from the N-terminal side in the amino acid sequence shown in SEQ ID NO: 3 is preferably leucine (Leu, L) or valine (Val, V). The 40th amino acid residue from the N-terminal side in the amino acid sequence shown in SEQ ID NO: 3 is preferably threonine (Thr, T) or serine (Ser, S). The 43rd amino acid residue from the N-terminal side in the amino acid sequence shown in SEQ ID NO: 3 is preferably valine (Val, V), isoleucine (Ile, I), or methionine (Met, M). The 44th amino acid residue from the N-terminal side in the amino acid sequence shown in SEQ ID NO: 3 is preferably tryptophan (Trp, W) or phenylalanine (Phe, F). The 45th amino acid residue from the N-terminal side in the amino acid sequence shown in SEQ ID NO: 3 is preferably aspartic acid (Asp, D) or glutamic acid (Glu, E). The 47th amino acid residue from the N-terminal side in the amino acid sequence shown in SEQ ID NO: 3 is preferably leucine (Leu, L), isoleucine (Ile, I), or methionine (Met, M). The 48th amino acid residue from the N-terminal side in the amino acid sequence shown in SEQ ID NO: 3 is preferably serine (Ser, S), threonine (Thr, T), or proline (Pro, P). The 49th amino acid residue from the N-terminal side in the amino acid sequence shown in SEQ ID NO: 3 is preferably asparagine (Asn, N) or serine (Ser, S). The 52" amino acid residue from the N-terminal side in the amino acid sequence shown in SEQ ID NO: 3 is preferably valine (Val, V) or alanine (Ala, A). The 55th amino acid residue from the N-terminal side in the amino acid sequence shown in SEQ ID NO: 3 is preferably leucine (Leu, L), valine (Val, V), isoleucine (Ile, I), or methionine (Met, M). The 56th amino acid residue from the N-terminal side in the amino acid sequence shown in SEQ ID NO: 3 is preferably isoleucine (Ile, I) or valine (Val, V). Preferably, an example of the consensus sequence comprising the amino acid sequence shown in SEQ ID NO: 3 is more specifically GXA(M/V/F)(S/A/T)R(A/S)(F/I/V)GDXXX(K/E)XXG(V/L)(I/V)XXP(E/Q/D)(I/V/F)X XXX(I/L/V)(T/S)XX(D/N/H)X(F/Y)(L/I/V/F)(V/L/I)(L/V)A(T/S)DG(V/I/M)(W/F)(D/E)X(L/I/M)(S/T/P)(N/S)XX(V/A)XX(L/V/I/M)(I/V). In such amino acid sequence, pluralities of amino acids in parentheses represent possible variations of amino acid residues at the relevant positions. Also, in the following amino acid sequences, "X" means that any amino acid residue may be present at the relevant position.

However, the 20th amino acid residue from the N-terminal side of the amino acid sequence shown in SEQ ID NO: 3 is more preferably alanine (Ala, A), serine (Ser, S) or cysteine (Cys, C). In addition, the 50th amino acid residue from the N-terminal side of the amino acid sequence shown in SEQ ID NO: 3 is more preferably aspartic acid (Asp, D), glutamic acid (Glu, E), lysine (Lys, K), glutamine (Gln, Q) or asparagine (Asn, N).

Variations in amino acid residues able to be adopted at prescribed locations is due to the reason indicated below. As is also described in Reference Document (1) ("McKee Biochemistry", 3rd edition, Chapter 5: Amino Acids, Peptides and Proteins, Section 5.1: Amino Acids, editor: Atsushi Ichikawa, translator: Shiniichi Fukuoka, publisher: Ryosuke Sone, publishing house: Kagaku-Dojin Publishing Company, INC, ISBN4-7598-0944-9), amino acids are well known to be classified according to side chains having similar properties (chemical properties or physical size). In addition, substitutions in terms of molecular evolution are well known to occur between amino acid residues classified in a prescribed group while retaining protein activity. On the basis of this concept, score matrices (BLOSUM) for mutation substitutions of amino acid residues are advocated in FIG. 2 of Reference Document (2) (Henikoff, S., Henikoff, J. G., Amino-acid substitution matrices from protein blocks, Proc. Natl. Acad. Sci. USA, 89, 10915-10919 (1992)), and these matrices are widely used. Reference Document (2) is based on the finding that amino acid substitutions of amino acid residues having side chains of similar chemical properties result in few structural or functional changes that affect the entire protein. According to Reference Documents (1) and (2), side chain groups of amino acids in terms of the multiple alignment can be determined on the basis of indicators such as chemical properties and physical sizes. According to the score matrices (BLOSUM) disclosed in Reference Document (2), amino acids having a score value of 0 or higher, and preferably amino acids having a score value of 1 or more, are indicated as a group. Typical groups include the 8 groups indicated below. Other detailed grouping may consist of a group of amino acids having a score value of 0 or higher, preferably a group of amino acids having a score value of 1 or higher, and more preferably a group of amino acids having a score value of 2 or higher.

1) Aliphatic Hydrophobic Amino Acid Group (ILMV Group)

This group is composed of a group of neutral, non-polar amino acids indicated in the above-mentioned Reference Document (1) that have an aliphatic hydrophobic side chain in the form of valine (Val, V), leucine (Leu, L), isoleucine (Ile, I) and methionine (Met, M). Among those amino acids classified as neutral non-polar amino acids according to Reference Document (1), FGACWP are not included in this group of aliphatic hydrophobic amino acids for the reason indicated below. Glycine (Gly, G) and alanine (Ala, A) are not classified in this group because of having a size equal to or smaller than a methyl group and having weak non-polar effects. Cysteine (Cys, C) is not classified in this group because it may play an important role in S—S bonding and has the characteristic of forming hydrogen bonds with oxygen atoms and nitrogen atoms. Phenylalanine (Phe, F) and tryptophan (Trp, W) are not classified in this group because they have side chains having a particularly high molecular weight and have strong aromatic effects. Proline (Pro, P) is not classified in this group because it demonstrates strong imino acid effects and the angle of the polypeptide side chain is fixed.

2) Hydroxymethylene Group-Containing Amino Acid Group (ST Group)

This group is a group of neutral polar amino acids having a hydroxymethylene group in a side chain thereof and is composed of serine (Ser, S) and threonine (Thr, T). Since hydroxyl groups present in the side chains of S and T are sugar bonding sites, there are many cases in which they are important sites since certain polypeptides (proteins) have a specific activity.

3) Acidic Amino Acids (DE Group)

This group is a group of amino acids having an acidic carboxyl group in a side chain thereof and is composed of aspartic acid (Asp, D) and glutamic acid (Glu, E).

4) Basic Amino Acids (KR Group)

This group is a group of basic amino acids and is composed of lysine (Lys, K) and arginine (Arg, R). K and R are positively charged over a wide pH range and have basic properties. On the other hand, histidine (His, H), which is classified as a basic amino acid, is hardly ionized at all at pH 7 and is not classified in this group.

5) Methylene Group-Polar Group (DHN Group)

This group has the characteristic of having a methylene group bonded as a side chain to all carbon atoms at the α position and having a polar group there beyond. The amino acids of this group have the characteristic in which the physical size of the non-polar group in the form of the methylene group is extremely similar, and this group is composed of asparagine (Asn, N, polar group is an amide group), aspartic acid (Asp, D, polar group is a carboxyl group) and histidine (His, H, polar group is an imidazole group).

6) Dimethylene Group-Polar Group (EKQR Group)

This group has the characteristic of having linear hydrocarbons equal to or larger than a dimethylene group bonded as a side chain to all carbons at the α position and having a polar group there beyond. The amino acids of this group have the characteristic of the physical size of the non-polar group in the form of the dimethylene group being extremely similar. This group is composed of glutamic acid (Glu, E), polar group is a carboxyl group), lysine (Lys, K, polar group is an amino group), glutamine (Gln, Q, polar group is an amido group) and arginine (Arg, R, polar group is an imino group and an amino group).

7) Aromatic Group (FYW Group)

This group contains aromatic amino acids having a benzene nucleus in a side chain thereof and is characterized by demonstrating uniquely aromatic chemical properties. This group is composed of phenylalanine (Phe, F), tyrosine (Tyr, Y) and tryptophan (Trp, W).

8) Cyclic and Polar Group (HY Group)

This group consists of amino acids simultaneously having a cyclic structure in a side chain thereof and polarity, and is composed of histidine (His, H, cyclic structure and polar group are both imidazole groups) and tyrosine (Tyr, Y, cyclic structure is a benzene nucleus and polar group is a hydroxyl group).

As has been described above, in the prescribed amino acid sequences shown in SEQ ID NO: 1 to 3, although the amino acid residue indicated as Xaa may be an arbitrary amino acid, it can also be understood that the amino acid residue indicated as Xaa may be substituted with an amino acid in the above-mentioned groups 1) to 8). Namely, in the present invention, the PP2C gene overexpressed in a plant may be any plant-derived PP2C gene provided it has three common sequences composed of the amino acid sequences shown in SEQ ID NO: 1 to 3 in order starting from the N-terminal side. Furthermore, an example of a PP2C gene has the amino acid sequence shown in SEQ ID NO: 4.

In addition, in the present invention, the gene may be a homologous gene of the previously exemplified genes. A homologous gene encodes a protein having PP2C activity. PP2C activity refers to $Mg^{2+}$- or $Mn^{2+}$-dependent serine/threonine phosphatase (Ser/Thr phosphatase) activity. Thus, whether or not a certain gene encodes a protein having PP2C activity is determined by examining whether or not it has serine/threonine phosphatase activity in the presence of $Mg^{2+}$ or $Mn^{2+}$. A conventionally known technique can be suitably used for the technique used to measure serine/threonine phosphatase activity. For example, a commercially available assay kit in the form of the ProFluor® Ser/Thr Phosphatase Assay Kit (Promega Corp.) can be used. An example of such a gene is a gene that encodes a protein that has PP2C activity and an amino acid sequence preferably having identity with the amino acid sequence represented by SEQ ID NO: 4 of 90% or more, more preferably 95% or more, even more preferably 97% or more, still more preferably 98% or more, and most preferably 99% or more.

(ANT Gene)

ANT gene is a gene that encodes ANT having the amino acid sequence represented by SEQ ID NO: 5. The product of ANT gene in the form of ANT is characterized according to the presence of an AP2 domain. This domain was initially identified in AP2 and is characterized by a region consisting of about 60 to 70 amino acid residues that has an extremely preserved core region having the ability to form an amphipathic α-helix and/or the ability to bind DNA (Jofuku, et al., Plant Cell 6: 1211-1225 (1994); Ohme-Takagi and Shinshi, Plant Cell 7: 173-182 (1995)). The full-length ANT protein has two AP2 domains (amino acids 281 to 357 and 383 to 451 of SEQ ID NO: 5) and a linker region (amino acids 358 to 382), and homology with respect to other AP2 domain proteins is limited to this region. The ANT gene of the present invention typically contains a coding region having a length of at least about 30 to 40 nucleotides to about 2500 nucleotides, and normally has a length of less than about 3000 nucleotides. Normally, the ANT gene of the present invention has a length of about 100 to about 5000 nucleotides and frequently has a length of about 500 to about 3000 nucleotides.

Furthermore, a gene that is functionally equivalent to ANT gene can also be used. Examples of such a gene include genes encoding a protein having an amino acid sequence preferably having identity with the amino acid sequence represented by SEQ ID NO: 5 of 90% or more, more preferably 95% or more, even more preferably 97% or more, still more preferably 98% or more and most preferably 99% or more.

(Vector)

The above-mentioned promoters and genes can be contained in a vector. Various regulatory elements may also be further linked thereto in a state in which they are able to function in the cells of a host plant. Preferable examples of such elements include terminators, drug resistance genes and enhancers. The fact that the type of expression vector and type of regulatory element can vary according to the host cells is a commonly known matter among persons skilled in the art. The vector of the present invention can further have a T-DNA region. The T-DNA region enhances the efficiency of gene introduction in the case of transforming a plant using *Agrobacterium* in particular.

The vector of the present invention can be produced using gene recombination technology commonly known among persons skilled in the art. Although a pBI vector or pUC vector, for example, is preferably used to construct a plant expression vector, the vector used is not limited thereto.

A method commonly known among persons skilled in the art, such as a method mediated by *Agrobacterium* or a method consisting of introducing directly into cells, can be used to introduce the plant expression vector into plant cells. Examples of methods medicated by *Agrobacterium* that can be used include the method of Nagel, et al. (FEMS Microbiol. Lett., 67, 325 (1990)). This method consists of first transforming *Agrobacterium* with the plant expression vector (by electroporation, for example), followed by introducing the transformed *Agrobacterium* into plant cells by a commonly known method such as the leaf disk method. Examples of methods for introducing a plant expression vector directly into cells include the electroporation method, particle gun method, calcium phosphate method and polyethylene glycol method. These methods are commonly known in the field, and a method that is suitable for the plant to be transformed can be suitably selected by a person skilled in the art. As will be subsequently described, cells introduced with a plant expression vector are selected based on kanamycin resistance or other drug resistance. The selected cells can be regenerated in a plant in accordance with ordinary methods.

Although there are no particular limitations thereon, examples of the plant of the present description include dicotyledons and monocotyledons, such as plants belonging to the Brassicaceae, Malvaceae, Gramineae, Solanaceae, Leguminosae or Salicaceae family (see below). Plants that grow rapidly, and are typically annuals, can be preferably used to increase production of phloem. An example of such a plant is the plant of the Malvaceae family such as *Hibiscus cannabinus*.

Brassicaceae: *Arabidopsis thaliana, Brassica rapa, Brassica napus, Brassica oleracea* var. *capitata, Brassica rapa* var. *pekinensis, Brassica rapa* var. *chinensis, Brassica rapa* var. *rapa*, *Brassica rapa* var. *hakabura*, *Brassica rapa* var. *lancinifolia*, *Brassica rapa* var. *peruviridis*, *Brassica rapa* var. *chinensis*, *Brassica Raphanus sativus*, *Wasabia japonica*, etc.

Solanaceae: *Nicotiana tabacum*, *Solanum melongena*, *Solaneum tuberosum*, *Lycopersicon lycopersicum*, *Capsicum annuum*, *Petunia*, etc.

Leguminosae: *Glycine max*, *Pisum sativum*, *Vicia faba*, *Wisteria floribunda*, *Arachis hypogaea*, *Lotus corniculatus* var. *japonicus*, *Phaseolus vulgaris*, *Vigna angularis*, *Acacia*, etc.

Asteraceae: *Chrysanthemum morifolium*, *Helianthus annuus*, etc.

Palmae: *Elaeis guineensis*, *Elaeis oleifera*, *Cocos nucifera*, *Phoenix dactylifera*, *Copernicia*, etc.

Anacardiaceae: *Rhus succedanea*, *Anacardium occidentale*, *Toxicodendron vernicifluum*, *Mangifera indica*, *Pistacia vera*, etc.

Cucurbitaceae: *Cucurbita maxima*, *Cucurbita moschata*, *Cucurbita pepo*, *Cucumis sativus*, *Trichosanthes cucumeroides*, *Lagenaria siceraria* var. *gourda*, etc.

Rosaceae: *Amygdalus communis*, *Rosa*, *Fragaria*, *Prunus*, *Malus pumila* var. *domestica*, etc.

Caryophyllaceae: *Dianthus caryophyllus*, etc.

Salicaceae: *Populus trichocarpa*, *Populus nigra*, *Populus tremula*, etc.

Gramineae: *Zea mays*, *Oryza sativa*, *Hordeum vulgare*, *Triticum aestivum*, *Phyllostachys*, *Saccharum officinarum*, *Pennisetum pupureum*, *Erianthus ravanae*, *Miscanthus virgatum*, *Sorghum*, *Panicum*, etc.

Lilaceae: *Tulipa*, *Lilium*, etc.

Myrtaceae: *Eucalyptus camaldulensis*, *Eucalyptus grandis*, etc.

Malvaceae: *Abelmoschus esculentus*, *Abutilon theophrasti*, *Althaea rosea*, *Gossypium* spp., *Hibiscus cannabinus*, *Malva moschata*, *Malvaviscus arboreus* var. *mexicanus*, *Pavonia hastata*, *Sida fallax*, etc.

Urticaceae: *Boehmeria nivea* var. *nipononivea*, *Boehmeria japonica*, *D. edulis*, *E. platyphyllum*, etc.

At least any of a cultivated plant individual, plant cells, plant tissue, callus and seed are included in the plant of the present description. In other words, those which are in a state that is able to ultimately be cultivated to a plant individual are all considered to be plants. In addition, various forms of plant cells are included in the above-mentioned plant cells. Examples of such plant cells include suspension cultured cells, protoplasts and leaf segments. A plant can be obtained by causing these plant cells to proliferate and differentiate. Furthermore, regeneration of a plant from plant cells can be carried out using a conventionally known method corresponding to the type of plant cells.

(Evaluation of Amount of Phloem Tissue)

In the present description, whether or not production of phloem tissue has increased can be evaluated according to, for example, the method indicated below. First, the height of each plant is measured. Next, the stem of each plant is cut at a prescribed location (such as 20 mm from the base) and the cut section is stained with a dye such as toluidine blue, methylene blue or hematoxylin. An image of the stained section is then captured and phloem area is determined by analyzing that image. The phloem area per cross-sectional area is then calculated to determine phloem ratio. Moreover, the increased phloem production effect is then determined from the above-mentioned plant height and phloem ratio. The increased phloem production effect is represented with the following equation using the ratio of the phloem area of the plant to the phloem area of a wild strain and the ratio of the height of the plant to the height of a wild strain.

Increased phloem production effect=(plant phloem area ratio)×(plant height ratio)

Whether or not production of phloem tissue has increased can be evaluated by comparing increased phloem production effects. An increased phloem production effect indicates an increase in the amount of phloem tissue.

The plant disclosed in the present description demonstrates a specific increase in phloem tissue. For example, the plant of the present disclosure preferably demonstrates an amount of phloem tissue (increased phloem production effect) that is preferably 2.0 times or more, more preferably 2.5 times or more, even more preferably 3.0 times or more, still more preferably 3.5 times or more and most preferably 4.0 times or more that of a wild strain. In addition, the plant of the present disclosure demonstrates phloem area that is preferably 1.6 times or more, more preferably 1.8 times or more, even more preferably 2.0 times or more, still more preferably 2.2 times or more and most preferably 2.5 times or more that of a wild strain. In addition, the plant of the present disclosure demonstrates height that is preferably 1.2 times or more, more preferably 1.3 times or more, even more preferably 1.5 times or more and still more preferably 1.6 times or more that of a wild strain.

In the plant disclosed in the present description, with respect to increased phloem production effect, the combination of promoter and cell growth-promoting gene is preferably SUC2 promoter and ANT gene or PP2C gene and more preferably SUC2 promoter and PP2C gene. In addition, an example of another combination is preferably TDR promoter and ANT gene or PP2C gene and more preferably TDR promoter and PP2C gene.

(Plant Production Method)

According to the disclosure of the present description, a method is provided for producing a plant having plant cells that retain a promoter that is specifically expressed in the vascular cambium or phloem cells of a plant, and a gene that encodes a protein that promotes cell growth under the control of the promoter. Details regarding the promoter and gene are as subsequently described. In addition, according to the production method disclosed in the present description, a plant can be obtained in which production of phloem tissue has been increased.

(Method for Increasing Production of Phloem Tissue)

According to the disclosure of the present description, a method for increasing production of phloem tissue is provided that includes a step of cultivating a plant having plant cells that retain a promoter that is specifically expressed in the vascular cambium or phloem cells of a plant, and a gene that encodes a protein that promotes cell growth under the control of the promoter. Details regarding the promoter and gene are as subsequently described. According to the production method disclosed in the present description, production of phloem tissue of a plant can be suitably increased. Increasing production of phloem tissue refers to increasing the weight of phloem tissue with respect to the total weight of the plant.

EXAMPLES

Although the following provides a detailed explanation of the present invention by indicating examples thereof, these do not limit the present invention.

Example 1

Acquisition of TDR and SUC2 Promoters

Young leaves of *Arabidopsis thaliana* (Col-0) were crushed after freezing with liquid nitrogen followed by extraction of genomic DNA using the DNeasy Plant Mini Kit (Qiagen Inc.). Using the prepare genomic DNA as template, each of the promoter regions of TDR (At5g61480) and SUC2 (At1g22710) of *Arabidopsis thaliana* was amplified by PCR. Each of the following primers provided with a restrictase site (HindIII or SalI), namely HindIII-TDR-F1 (SEQ ID NO: 8) and TDR-SalI-R1 (SEQ ID NO: 9) as TDR promoter amplification primers and HindIII-SUC2-F1 (SEQ ID NO: 10 and SUC2-SalI-R1 (SEQ ID NO: 11) as SUC2 promoter amplification primers, were used.

```
HindIII-TDR-F1:
                                        (SEQ ID NO: 8)
TATGACCATGATTACGCCAAGCTTAAGAAGTTGATTTTGGAC TDR-SalI-R1:
                                        (SEQ ID NO: 9)
ACCCGGGGATCCTCTAGAGTCGACCGTAGCTTTTAGAAAGAA HindIII-SUC2-F1:
                                        (SEQ ID NO: 10)
TATGACCATGATTACGCCAAGCTTACGCAAACTAACTACAAC SUC2-SalI-R1:
                                        (SEQ ID NO: 11)
ACCCGGGGATCCTCTAGAGTCGACATTTGACAAACCAAGAAA
```

(Production of Promoter Cloning Vector pBI101N2)

Plant expression vector pBI121 (Clontech Inc.) was treated with restrictases HindIII and BamHI. Next, equal amounts of oligonucleotides (Linker-F2 (SEQ ID NO: 12) and Linker-R2 (SEQ ID NO: 13)) were mixed followed by allowing to stand for 10 minutes at 96° C. and then for 2 hours at room temperature. After standing, a ligation reaction was carried out with the oligonucleotide mixture, the above-mentioned restrictase-treated pBI121 and the Mighty Mix DNA ligation kit (Takara Bio Inc.) to produce promoter cloning vector pBI101N2.

```
Linker-F2:
                                        (SEQ ID NO: 12)
AGCTTGGCGCGCCTTAATTAAACTAGTCTCGAGGTCGACT Linker-R2:
                                        (SEQ ID NO: 13)
CTAGAGTCGACCTCGAGACTAGTTTAATTAAGGCGCGCCA
```

The amplified TDR promoter and SUC2 promoter were cloned to the produced vector pBI101N2 using the In-Fusion® Dry-Down PCR Cloning Kit w/Cloning Enhancer to produce promoter cloning vectors pBI TDR and pBI SUC2.

(Production of Plant Expression Vectors pBI TDR:PP2C and pBI TDR:ANT)

Using genomic DNA prepared from *Arabidopsis thaliana* (Col-0) as template, *Arabidopsis thaliana* PP2C (At3G05640) gene was amplified by PCR to produce vector pBI 35SΩ:PP2C. In addition, using cDNA of *Arabidopsis thaliana* (Col-0) as template, *Arabidopsis thaliana* ANT (At4G37750) gene was amplified by PCR to produce vector pBI 35SΩ:ANT. The PCR reaction was carried out using SalI-PP2C-F (SEQ ID NO: 14) and PP2C-BsrGI-R (SEQ ID NO: 15) as PP2C amplification primers provided with a restrictase site (SalI or BsrGI), and using SalI-ANT-F (SEQ ID NO: 16) and ANT-BsrGI-R (SEQ ID NO: 17) as ANT amplification primers.

```
SalI-PP2C-F:
                                        (SEQ ID NO: 14)
AATTACTATTTACAATTACAGTCGACATGGGACATTTCTCTTCCATG

PP2C-BsrGI-R:
                                        (SEQ ID NO: 15)
CGGGCGGCCGCTTTACTTGTACACTATAGAGATGGCGACGACG

SalI-ANT-F:
                                        (SEQ ID NO: 16)
AATTACTATTTACAATTACAGTCGACATGAAGTCTTTTTGTGATAATGA
TGATAATAATCAT

ANT-BsrGI-R:
                                        (SEQ ID NO: 17)
AGCCGGGCGGCCGCTTTACTTGTACATCAAGAATCAGCCCAAGCAGCG
```

The plasmid DNA produced as described above was used as template and amplified by carrying out PCR reactions using each of the primers indicated below. TDR-SalI-PP2C-F1 (SEQ ID NO: 18) and PPC2-SacI-RI (SEQ ID NO: 19) were used as primers for amplifying TDR:PPC2, and TDR-SalI-ANT-F1 (SEQ ID NO: 20) and ANT-SacI-R1 (SEQ ID NO: 21) were used as primers for amplifying TDR:ANT. Next, the amplified genes were cloned to a promoter cloning vector treated with SalI and SacI using the In-Fusion® Dry-Down PCR Cloning Kit w/Cloning Enhancer to produce plant expression vectors pBI TDR:PP2C and pBI TDR:ANT.

```
TDR-SalI-PP2C-F1:
                                        (SEQ ID NO: 18)
TTCTTTCTAAAAGCTACGGTCGACATGGGACATTTCTCTTCC

PP2C-SacI-RI:
                                        (SEQ ID NO: 19)
GAACGATCGGGGAAATTCGAGCTCCTATAGAGATGGCGACGA

TDR-SalI-ANT-F1:
                                        (SEQ ID NO: 20)
TTCTTTCTAAAAGCTACGGTCGACATGAAGTCTTTTTGTGAT

ANT-SacI-R1:
                                        (SEQ ID NO: 21)
GAACGATCGGGGAAATTCGAGCTCTCAAGAATCAGCCCAAGC
```

(Production of Plant Expression Vectors pBI SUC2:PP2C and pBI SUC2:ANT)

Plasmid DNA was used as template and amplified by carrying out PCR reactions using each of the primers indicated below in the same manner as in the case described above. SUC2-SalI-PPC2-F1 (SEQ ID NO: 22) and PP2C-SacI-R1 (SEQ ID NO: 23) were used as primers for amplifying SUC2:PP2C and SUC2-SalI-ANT-F1 (SEQ ID NO: 24) and ANT-SacI-R1 (SEQ ID NO: 25) were used as primers for amplifying SUC2:ANT. Next, the amplified genes were cloned in the same manner as in the case described above to produce plant expression vectors pBI SUC2:PP2C and pBI SUC2:ANT.

```
SUC2-SalI-PP2C-F1:
                                        (SEQ ID NO: 22)
TTTCTTGGTTTGTCAAATGTCGACATGGGACATTTCTCTTCC

PP2C-SacI-R1:
                                        (SEQ ID NO: 23)
GAACGATCGGGGAAATTCGAGCTCCTATAGAGATGGCGACGA
```

-continued

SUC2-SalI-ANT-F1:
(SEQ ID NO: 24)
TTTCTTGGTTTGTCAAATGTCGACATGAAGTCTTTTTGTGAT

ANT-SacI-R1:
(SEQ ID NO: 25)
GAACGATCGGGGAAATTCGAGCTCTCAAGAATCAGCCCAAGC

Example 2

Production of Transformants of Wild Strain *Arabidopsis thaliana* (Col-0)

The vectors produced as described above (pBI 35SΩ: PP2C, pBI SUC2:PP2C, pBI TDR:PP2C, pBI 35SΩ:ANT, pBI SUC2:ANT and pBI TDR:ANT) were transformed to wild-type *Arabidopsis thaliana* (Col-0) using floral dip transformation to produce six types of transformants (strains 35SΩ:PP2C, SUC2:PP2C, TDR:PP2C, 35SΩ:ANT, SUC2: ANT and TDR:ANT). Wild-type *Arabidopsis thaliana* and the above-mentioned transformants were grown in MS medium containing kanamycin (final concentration: 30 μg/mL) and carbenicillin (final concentration: 100 μg/mL) followed by screening the T1 plants. Subsequently, the plants were potted using Supermix A (Sakata Seed Corp.). The plants were cultivated in a cultivation room (22° C., 16-hour lighting conditions (approx. 50 μmol·m$^{-2}$·s$^{-1}$ white fluorescent light)/8 hour darkness conditions, humidity 60%) to acquire T2 seeds.

Example 3

Evaluation of Increased Production of Phloem Tissue

After vernalizing the T2 seeds for 3 days, the seeds were sowed directly using Supermix A. The height of each *Arabidopsis thaliana* plant was measured after cultivating for 9 weeks. Next, inflorescence stem samples obtained by cutting the first inflorescence stem 20 mm from the base were embedded in 5% agarose. Subsequently, the central portions of the embedded inflorescence stem samples (corresponding to an area 20 mm from the base of the first inflorescence stem) were sliced at a thickness of 100 μm with a Microslicer (Model DTK-1000 (Dosaka EM Co., Ltd.) to produce sections. These cross-sections of the inflorescence stems were stained with 0.05% (w/v) toluidine blue for 1 minute at room temperature and rinsed followed by observing under a microscope. Images of cross-sectional photographs were processed using Adobe Photoshop followed by extraction of phloem tissue present in vascular tissue. The diameter of the inflorescence stem, cross-sectional area and phloem area were measured using Paint.NET. In addition, phloem ratio was determined as the phloem area per cross-sectional area.

FIG. 1 shows cross-sectional photographs of the stems of wild strain (Col-0) and strains TDR:PP2C and TDR:ANT (top) and images of phloem tissue in stem cross-sections (bottom).

Figure 2:
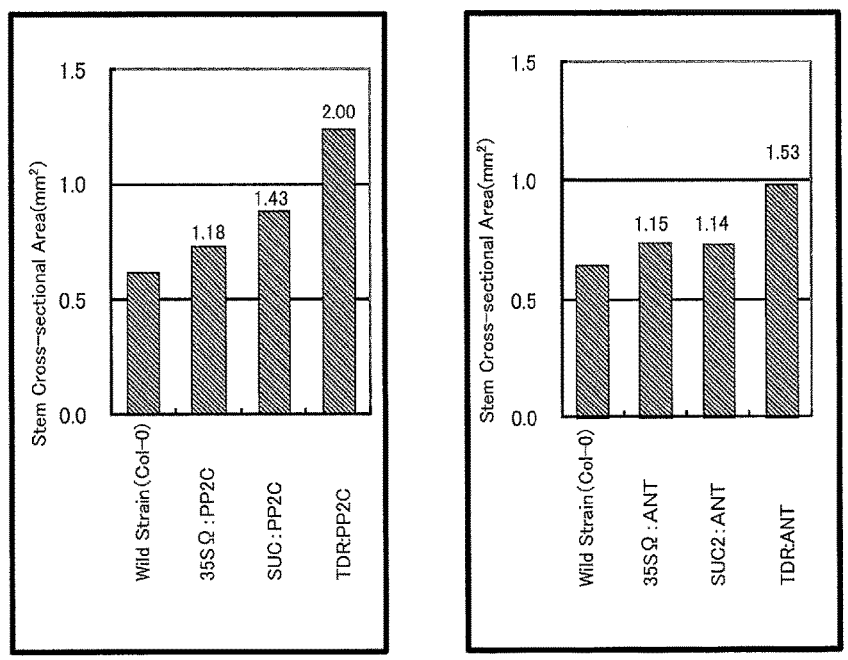
FIG. 2 shows cross-sectional areas of the stems of wild strain *Arabidopsis thaliana* (Col-0), strain 35SΩ:PP2C, strain SUC2:PP2C, strain TDR:PP2C, strain 35SΩ:ANT, strain SUC2:ANT and strain TDR:ANT.

FIG. 2 indicates the stem cross-sectional areas of the wild strain and each transformant. Furthermore, each of the values depicted near the graphs of each transformant in FIG. 2 indicates the ratio of the stem cross-sectional area of each transformant to the stem cross-sectional area of the wild strain. The stem cross-sectional area of strain SUC2:PP2C was 1.3 times or more the stem cross-sectional area of the wild strain. The stem cross-sectional area of strain TDR: ANT was 1.5 times or more the stem cross-sectional area of the wild strain. The stem cross-sectional area of strain TDR:PP2C was 1.8 times or more and 2.0 times or more the stem cross-section area of the wild strain.

Figure 3:
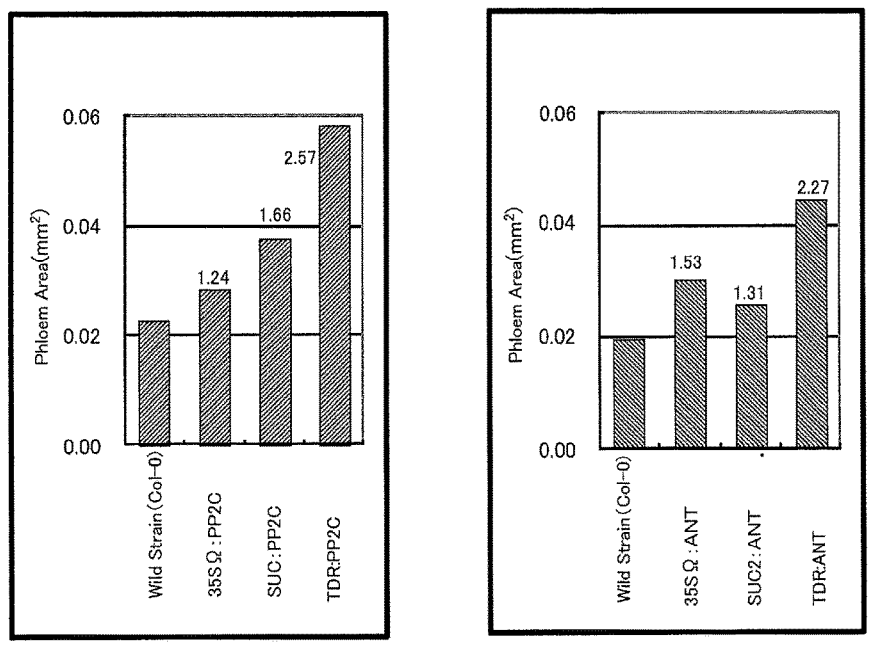
FIG. 3 shows phloem areas of the stems of wild strain *Arabidopsis thaliana* (Col-0), strain 35SΩ:PP2C, strain SUC2:PP2C, strain TDR:PP2C, strain 35SΩ:ANT, strain SUC2:ANT and strain TDR:ANT.

FIG. 3 indicates the phloem areas of the wild strain and each transformant. Furthermore, each of the values depicted near the graphs of each transformant in FIG. 3 indicates the ratio of phloem area of each transformant to the phloem area of the wild strain. The phloem area of strain SUC2:PP2C was 1.6 times or more the phloem area of the wild strain. The phloem area of strain TDR:ANT was 1.8 times or more, 2.0 times or more and 2.2 times or more the phloem area of the wild strain. The phloem area of strain TDR:PP2C was 2.5 times or more the phloem area of the wild strain.

As shown in FIG. 2, TDR promoter and SUC2 promoter were determined to have considerable increasing effects with respect to steam cross-sectional area in comparison with 35SΩ promoter. Those effects were determined to be particularly high for TDR promoter. In addition, although ANT and PP2C also contribute to increased steam cross-sectional area, PP2C was determined to have a more potent effect.

As shown in FIG. 3, TDR promoter and SUC2 promoter were determined to have considerable increasing effects with respect to phloem area in comparison with 35SΩ promoter. Those effects were determined to be particularly high for TDR promoter. The effect of increasing phloem area was more prominent than the effect of increasing stem cross-sectional area. In addition, although ANT and PP2C also contribute to increased phloem area, PP2C was determined to have a more potent effect.

Figure 4:
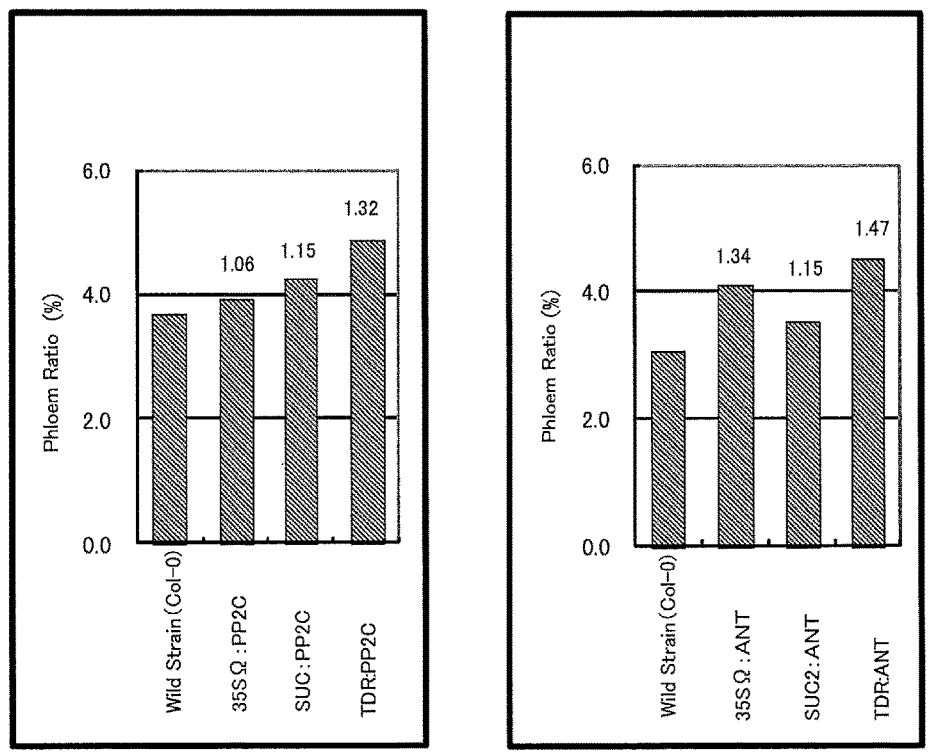
FIG. 4 shows phloem ratios of the stems of wild strain *Arabidopsis thaliana* (Col-0), strain 35SΩ:PP2C, strain SUC2:PP2C, strain TDR:PP2C, strain 35SΩ:ANT, strain SUC2:ANT and strain TDR:ANT.

FIG. 4 indicates the phloem ratios of the wild strain and each transformant. Furthermore, each of the values depicted near the graphs of each transformant in FIG. 4 indicates the ratio of phloem ratio of each transformant to the phloem ratio of the wild strain. The phloem ratio of strain TDR:ANT was 1.4 times or more the phloem ratio of the wild strain. As shown in FIG. 4, TDR promoter and SUC2 promoter were determined to have considerable increasing effects with respect to phloem ratio in comparison with 35SΩ promoter. Those effects were determined to be particularly high for TDR promoter. In addition, although ANT and PP2C also contribute to increased phloem ratio, PP2C was determined to have a more potent effect.

Figure 5:
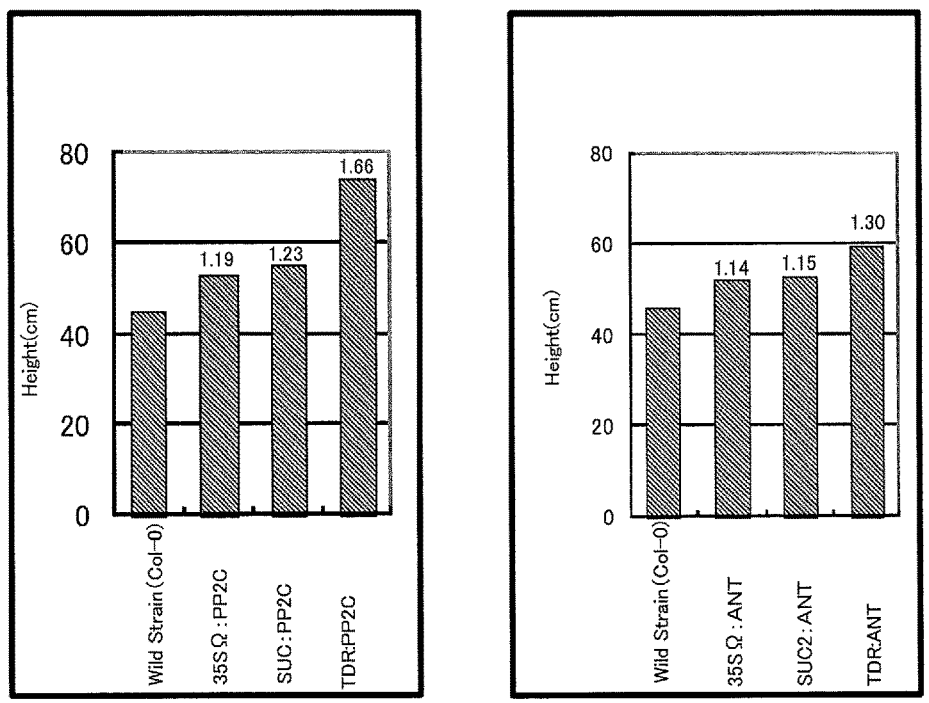
FIG. 5 shows the heights of wild strain *Arabidopsis thaliana* (Col-0), strain 35SΩPP2C, strain SUC2:PP2C, strain TDR:PP2C, strain 35SΩ:ANT, strain SUC2:ANT and strain TDR:ANT.

FIG. 5 indicates the heights of the wild strain and each transformant. Furthermore, each of the values depicted near the graphs of each transformant in FIG. 5 indicates the ratio of the height of each transformant to the height of the wild strain. The height of strain TDR:ANT was 1.3 times or more the height of the wild strain. The height of strain TDR:PP2C was 1.5 times or more and 1.6 times or more the height of the wild strain. The height of each transformant was higher than that of the wild strain. As shown in FIG. 5, TDR promoter and SUC2 promoter were determined to have considerable increasing effects with respect to height in comparison with 35SΩ promoter. Those effects were determined to be particularly high for TDR promoter. In addition, although ANT and PP2C also contribute to increased height, PPC2 was determined to have a more potent effect. In this manner, not only increased phloem area, but also greater height, is an effect that cannot be predicted by a person skilled in the art.

Next, the results of comparing the increased phloem production effects of each transformant are shown in Table 1. As shown in Table 1, the increased phloem production effect of strain SUC2:PP2C was 2.0 times or more. The increased phloem production effect of strain TDR:ANT was 2.5 times or more. The increased phloem production effect of strain TDR:PP2 was 3.0 times or more, 3.5 times or more, and 4.0 times or more. On the basis of these results, introduction of PP2C gene or ANT gene under the control of TDR or SUC2 promoter was determined to dramatically enhance phloem increased production effect. In addition, the increased phloem production effect of TDR promoter was determined to be greater than that of SUC2 promoter, and the increased phloem production effect of PP2C gene was determined to be greater than that of ANT gene.

TABLE 1

| Type | Phloem Increased Production Effect |
| --- | --- |
| Wild type strain (Col-0) | 1 |
| 35SΩ:PP2C strain | 1.5 |

TABLE 1-continued

| Type | Phloem Increased Production Effect |
| --- | --- |
| SUC2:PP2C strain | 2 |
| TDR:PP2C strain | 4.3 |
| 35SΩ:ANT strain | 1.7 |
| SUC2:ANT strain | 1.5 |
| TDR:ANT strain | 2.9 |

[Sequence Listing Free Text]

SEQ ID NOS: 1 to 3: Consensus sequences in protein phosphatases

SEQ ID NOS: 8 to 25: Primers

[Sequence Listings]

What is claimed is:

1. A method of producing a transformed plant, the method comprising:
   (a) transforming a host plant cell with a DNA construct, wherein the DNA construct comprises a heterologous promoter that consists of the nucleic acid sequence of SEQ ID NO: 6 and said heterologous promoter is operably linked to (i) a nucleotide sequence encoding a protein phosphatase 2C (PP2C) protein from *Arabidopsis* and having at least 95% amino acid sequence identity to SEQ ID NO: 4 or (ii) a nucleotide sequence encoding an aintegumenta (ANT) protein from *Arabidopsis* and having at least 95% amino acid sequence identity to SEQ ID NO: 5;
   (b) generating from said plant cell a transformed plant in which said DNA construct is expressed to overexpress said PP2C protein or ANT protein and obtaining a plurality of said transformed plants; and
   (c) selecting from said plurality of said transformed plants a transformed plant having an increased phloem production effect by at least 2 times or more as compared to a wild type plant of the same species lacking said DNA construct and grown under the same conditions, and wherein said increase in phloem production effect is represented with an equation of A×B, wherein A represents a ratio of a phloem area of a stem at a prescribed location of the selected transformed plant to a phloem area of a stem at the prescribed location of a wild type plant of the same species lacking said DNA construct, and B represents a ratio of the height of the selected transformed plant to a wild type plant of the same species lacking said DNA construct.

2. The method of claim 1, wherein said PP2C protein has the amino acid sequence of SEQ ID NO: 4.

3. The method of claim 1, wherein said ANT protein has the amino acid sequence of SEQ ID NO: 5.

4. The method according to claim 1, wherein the transformed plant is a dicotyledon.

5. The method according to claim 4, wherein the transformed plant is a plant of the Brassicaceae family.

6. The method according to claim 1, wherein the transformed plant is a monocotyledon.

7. The method according to claim 6, wherein the transformed plant is a plant of the Gramineae family.

8. The method according to claim 1, wherein the transformed plant is a plant of the Malvaceae family.

* * * * *